(12) United States Patent
Katsuki

(10) Patent No.: US 9,357,960 B2
(45) Date of Patent: Jun. 7, 2016

(54) MONITORING DEVICE AND MONITORING METHOD

(71) Applicant: Arkray, Inc., Kyoto-shi, Kyoto (JP)

(72) Inventor: Koji Katsuki, Kyoto (JP)

(73) Assignee: ARKRAY, INC., Kyoto (JP)

( * ) Notice: Subject to any disclaimer, the term of this patent is extended or adjusted under 35 U.S.C. 154(b) by 87 days.

(21) Appl. No.: 14/560,378

(22) Filed: Dec. 4, 2014

(65) Prior Publication Data

US 2015/0087941 A1 Mar. 26, 2015

Related U.S. Application Data

(62) Division of application No. 13/009,295, filed on Jan. 19, 2011, now Pat. No. 8,923,946.

(30) Foreign Application Priority Data

Jan. 19, 2010 (JP) .................................. 2010-009472
Dec. 7, 2010 (JP) .................................. 2010-272492

(51) Int. Cl.
*A61B 5/00* (2006.01)
*A61B 5/1495* (2006.01)
*A61B 5/145* (2006.01)
(Continued)

(52) U.S. Cl.
CPC .............. *A61B 5/1495* (2013.01); *A61B 5/1473* (2013.01); *A61B 5/1491* (2013.01); *A61B 5/14503* (2013.01); *A61B 5/14532* (2013.01); *A61B 5/14865* (2013.01);
(Continued)

(58) Field of Classification Search
CPC ............... A61B 5/1491; A61B 5/1495; A61B 5/14532; A61B 5/14865; A61B 5/14503; A61B 5/6849
USPC .......................................... 600/345; 205/792
See application file for complete search history.

(56) References Cited

U.S. PATENT DOCUMENTS 6,560,471 B1 5/2003 Heller et al.
2003/0083558 A1 5/2003 Skover
(Continued)

FOREIGN PATENT DOCUMENTS

JP 53-122942 10/1978
JP 55-37700 3/1980
(Continued)

OTHER PUBLICATIONS

European Search Report dated May 25, 2011 issued to European application No. EP 11 15 1349.
(Continued)

*Primary Examiner* — Christian Jang
(74) *Attorney, Agent, or Firm* — Knobbe, Martens, Olson & Bear, LLP

(57) ABSTRACT

A monitoring device which measures numerical value information on a subject substance in a body fluid has an electrochemical sensor including a sensor unit for detecting the subject substance which is used in the way of being embedded subcutaneously and generating an electric signal correlating to the numerical value information on the subject substance, and a temperature control unit which adjusts the detected ambient temperature as a temperature ambient to a sensor unit when detecting the subject substance so as to reach a target setting temperature when measuring the subject substance.

7 Claims, 26 Drawing Sheets

(51) Int. Cl.
*A61B 5/1486* (2006.01)
*A61B 5/1491* (2006.01)
*A61B 5/1473* (2006.01)

(52) U.S. Cl.
CPC ...... *A61B 5/6849* (2013.01); *A61B 2560/0252* (2013.01); *A61B 2562/0271* (2013.01)

(56) References Cited

U.S. PATENT DOCUMENTS

| | | |
|---|---|---|
| 2003/0100821 A1 | 5/2003 | Heller et al. |
| 2006/0222566 A1 | 10/2006 | Brauker et al. |
| 2008/0269584 A1 | 10/2008 | Shekalim |
| 2009/0030641 A1 | 1/2009 | Fjield et al. |
| 2009/0098657 A1 | 4/2009 | Blais et al. |

FOREIGN PATENT DOCUMENTS

| | | |
|---|---|---|
| JP | 07-014664 | 1/1995 |
| JP | 2002-025757 | 1/2002 |
| JP | 2002-090357 | 3/2002 |
| JP | 2007-209523 | 8/2007 |
| JP | 4324673 | 6/2009 |
| JP | 2010-162189 | 7/2010 |
| WO | WO 02/058537 | 8/2002 |
| WO | WO 03/003915 | 1/2003 |
| WO | WO 2008/114224 | 9/2008 |

OTHER PUBLICATIONS

Office Action issued in Japanese Patent Application No. 2010-272492, mailed Nov. 5, 2013.

MONITORING DEVICE AND MONITORING METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The disclosures of U.S. application Ser. No. 13/009,295, filed Jan. 19, 2011 and Japanese patent applications No. JP2010-009472 filed on Jan. 19, 2010 and No. JP2010-272492 filed on Dec. 7, 2010 including the specification, drawings and abstract are incorporated herein by reference.

TECHNICAL FIELD

The present invention relates to a monitoring device for and a monitoring method of measuring numerical value information on a subject substance in a body fluid.

BACKGROUND OF THE INVENTION

A conventional known technology is a technology of measuring the numerical value information on the subject substance in the body fluid, e.g., measuring continuously a glucose concentration in an interstitial liquid of the examinee by employing an electrochemical sensor embedded in an abdomen region and an arm region of the examinee. The electrochemical sensor is a sensor capable of detecting a minute amount of electric current by making use of electrochemical reaction, and is suited to detecting a minute amount of chemical substance in which oxidation-reduction reaction occurs.

The electrochemical sensor for measuring the glucose concentration involves using, in many cases, a biosensor which detects the subject substance by utilizing enzyme reaction in a way that immobilizes the enzyme to a sensor unit so disposed as to be embedded subcutaneously. This type of biosensor normally has a working electrode and a counter electrode, in which the enzyme (e.g., glucose oxidase) is immobilized to the working electrode. The glucose concentration can be measured based on, with a constant voltage (e.g., approximately 0.3V-0.6V) being consecutively applied to between the working electrode and the counter electrode, a response current obtained at this point of time.

The glucose oxidase produces gluconic acid by selectively reacting on the glucose under an existence of oxygen. On this occasion, the oxygen is reduced, while hydrogen peroxide proportional to a quantity of the glucose is generated. The hydrogen peroxide can be oxidized electrochemically easily and can be therefore measured by use of a pair of electrodes. Namely, the response current value can be obtained by the electrochemically oxidizing the hydrogen peroxide generated by the enzyme reaction of the enzyme as described above. Then, the glucose concentration can be calculated based on a sampling current obtained by periodically sampling the electric current from the continuously acquired response current values.

An activity of the enzyme, however, fluctuates depending on a reaction temperature. By contrast, a subcutaneous temperature largely fluctuates depending on a change in heat up temperature environment surrounding the examinee such as a living environment (e.g., an outdoor air temperature) of the examinee and activities in daily living (typified by bathing and taking excises) thereof. Therefore, in the case of continuously measuring the glucose concentration over a comparatively long period of time by use of the subcutaneous-embedding type of electrochemical sensor, a measurement result thereof is easily affected particularly by the change in heat up temperature environment.

Hence, in the case of measuring the glucose concentration by employing the subcutaneous-embedding type of electrochemical sensor, there is proposed a technology of measuring a temperature ambient to the sensor unit as the reaction temperature and correcting a calculated value corresponding to the measured temperature (refer to U.S. Pat. No. 6,560,471).

This type of temperature correction is normally conducted by use of temperature correction data indicating temperature dependency that is empirically obtained beforehand. The temperature correction data is used for determining a correction quantity and a correction coefficient on the basis of a temperature difference between a normal temperature and an ambient temperature in a way that sets the normal temperature (e.g., about 25° C.) as a reference temperature and for canceling the influence caused by the change in heat up temperature environment surrounding the examinee on the basis of this correction quantity.

SUMMARY OF THE INVENTION

As by the prior art, however, in the case of correcting the measurement value obtained from the electrochemical sensor by use of, e.g., a temperature correction algorithm, this temperature correction algorithm becomes highly complicated in many cases, accurate cancellation of the influence accompanying the fluctuation in the heat up temperature environment when performing the measurement involves a difficulty. Hence, according to the prior art, there exist actual circumstances in which it is difficult to sufficiently enhance reliability and reproducibility of the measurement result of the subject substance.

It is an object of the present invention, which was devised under the actual circumstances described above, to provide a technology capable of obtaining the measurement result exhibiting the high reliability and the high reproducibility under a state where a change in heat up temperature environment occurs on the occasion of measuring numerical value information on a subject substance in a body fluid.

The following means is adopted for accomplishing the object described above. A monitoring device according to the present invention, which measures numerical value information on a subject substance in a body fluid, includes: an electrochemical sensor including a sensor unit for detecting the subject substance which is used in the way of being embedded subcutaneously and generating an electric signal correlating to the numerical value information on the subject substance; and a temperature control unit including a temperature sensor which measures a temperature (this temperature contains a "detected ambient temperature" itself) correlating to a detected ambient temperature defined as a temperature ambient to the sensor unit and a temperature adjusting element which adjusts the detected ambient temperature, and adjusting the detected ambient temperature so as to reach a target setting temperature when measuring the subject substance by controlling an operation state of the temperature adjusting element on the basis of the temperature measured by the temperature sensor.

As described above, the electrochemical sensor according to the present invention is disposed in such a way that the sensor unit for detecting the subject substance is embedded subcutaneously. This sensor unit is formed on a part of, e.g. a base material and may retain a living organism based material such as the enzyme causing the enzyme reaction with the subject substance. The electrochemical sensor may be used in a mode where the sensor unit is disposed subcutaneously, and, as a matter of course, the whole electrochemical sensor including the base material does not need disposing subcutaneously. Accordingly, for instance, the sensor unit is formed on a front end side of the base material, in which case a proximal end of the base material may be so disposed as to be exposed from the surface of the skin.

Further, the subject substance in the body fluid can be exemplified such as glucose and lactic acid. Then, the numerical value information on the subject substance has a concept of embracing the numerical value information for quantitatively evaluating the subject substance such as measuring a concentration and a quantity of the subject substance and, in addition, the numerical value information for evaluating the subject substance qualitatively such as detecting whether or not the subject substance exists within a detection target region or exceeds a certain level.

According to the present invention, when detecting the subject substance, the temperature control unit adjusts the detected ambient temperature defined as the temperature ambient to the sensor unit so as to reach the target setting temperature. This target setting temperature has a role as the target temperature of the detected ambient temperature when the sensor unit detects the subject substance and is a temperature considered so that its influence is not exerted on the measurement result even when the heat up temperature environment fluctuates as the external ambient temperature fluctuates so far as the subject substance is measured in a state where the detected ambient temperature is kept in the vicinity of this temperature. The target setting temperature can be previously set within a range of, e.g., the normal temperature. Note that in the case of continuously measuring the subject substance repeatedly at an interval of a fixed period of time by way of one example of the mode of using the electrochemical sensor, the measurement period and the measurement standby period of the subject substance occur alternately, thereby forming the measurement cycle. According to the present invention, at least during the measurement period of the subject substance, the detected ambient temperature may be controlled to the target setting temperature. Namely, the detected ambient temperature during the measurement standby period of the subject substance may be or may not be coincident with the target setting temperature.

According to the present invention, under a state where the heat up temperature environment changes also, on the occasion of measuring the numerical value information on the subject substance in the body fluid, the detected ambient temperature can be kept at a temperature equal to the target setting temperature or at a temperature that is sufficiently approximate to the target setting temperature. Namely, the detected ambient temperature is maintained at the temperature equal to the target setting temperature, in which state the subject substance can be detected. Therefore, for example, even when the heat up temperature environment surrounding the examinee changes, it is feasible to restrain the influence thereof from being exerted on the measurement result. Furthermore, according to the present invention, the electric signal (e.g., a value of a response current flowing to between electrodes of the sensor unit) correlating to the numerical value information on the subject substance that is generated by the electrochemical sensor does not need undergoing a temperature correction process corresponding to the heat up temperature environment when performing the measurement. Accordingly, even under the state where the heat up temperature environment changes, it is possible to preferably improve the reliability and the reproducibility of the measurement result of the numerical value information on the subject substance in the body fluid.

The monitoring device according to the present invention can be attached to the examinee. Further, this temperature adjusting element may also be a Peltier device. The Peltier device is one type of a thermoelectric transducer (material), in which when inverting a polarity of the electric current flowing to a closed circuit formed by joining two types of conductors or semiconductors, a relation between an exothermic portion and an endothermic portion is reversed. The operation state of the temperature adjusting element is controlled corresponding to the measurement result of the temperature measured by the temperature sensor, whereby the detected ambient temperature can be kept at the target setting temperature with high accuracy.

The monitoring device according to the present invention can further include a sensor control unit which controls the electrochemical sensor. In this case, each of the temperature sensor, the temperature adjusting element and the temperature control unit may be disposed in a housing accommodating the sensor control unit or in the electrochemical sensor. Moreover, the sensor control unit may further calculate numerical value information on the subject substance on the basis of an electric signal generated by the electrochemical sensor.

Moreover, the monitoring device can further include a result display unit for acquiring the calculation result of the sensor control unit and displaying the calculation result. In this case, each of the temperature sensor, the temperature adjusting element and the temperature control unit may be disposed in at least any one of the housing accommodating the sensor control unit, the electrochemical sensor and the housing provided with the result display unit. Further, the subject substance in the body fluid is the interstitial liquid or the glucose in the blood, and the monitoring device can measure the concentration of the glucose.

Moreover, the temperature control unit may adjust the detected ambient temperature so as to reach a standby target setting temperature that is set lower than the target setting temperature when standing by for measuring the subject substance.

Further, the temperature control unit may acquire first numerical value information defined as the numerical value information on the subject substance measured by use of the electrochemical sensor and second numerical value information defined as the numerical value information on the subject substance measured by a second monitoring device in a way that uses a body fluid sampled in vitro from an examinee, and may change, if a difference between the first numerical value information and the second numerical value information exceeds a predetermined first threshold value, a setting value of the target setting temperature when measuring the subject substance.

Still further, the temperature control unit, in the case of adjusting the detected ambient temperature so as to reach the standby target setting temperature when standing by for measuring the subject substance, may acquire the first numerical value information and the second numerical value information, and may change, if the difference between the first numerical value information and the second numerical value information exceeds a predetermined second threshold value, the setting value of the standby target setting temperature, on a low-temperature side, when standing by for measuring the subject substance.

Yet further, the temperature control unit may acquire, with respect to the first numerical value information and the second numerical value information, each of the numerical value information corresponding to first timing after the monitoring device has started the measurement and the numerical value information corresponding to second timing that traces back to just a predetermined period from the first timing. Then, the temperature control unit may change, if a difference between the second numerical value information at the first timing and the second numerical value information at the second timing is within a predetermined third threshold value and if a difference between the first numerical value information at the first timing and the first numerical value information at the second timing exceeds a predetermined fourth threshold value, the setting value of the target setting temperature when measuring the subject substance.

Moreover, the temperature control unit may change, in the case of adjusting the detected ambient temperature so as to reach the standby target setting temperature when standing by for measuring the subject substance and if an elapse period reaching the first timing since the start of the measurement exceeds a predetermined reference period, the setting value of the standby target setting temperature, on the low-temperature side, when standing by for measuring the subject substance.

Further, the present invention can be grasped by way of a monitoring system which measures the numerical value information on the subject substance, a monitoring method of measuring the numerical value information on the subject substance, a program and a recording medium recorded with this program.

Herein, a monitoring method according to the present invention by which a monitoring device having an electrochemical sensor including a sensor unit, for detecting a subject substance in a body fluid, disposed in the way of being embedded subcutaneously, measures numerical value information on the subject substance, includes a step of adjusting a detected ambient temperature defined as a temperature ambient to the sensor unit so as to reach a target setting temperature when measuring the subject substance.

Then, the monitoring method according to the present invention may further include: a temperature acquiring step of acquiring a measurement result of a temperature sensor which measures a temperature correlating to the detected ambient temperature defined as the temperature ambient to the sensor unit when measuring the subject substance; a determining step of comparing the acquired temperature acquired in the temperature acquiring step with a target setting temperature and determining whether a temperature difference between the acquired temperature and the target setting temperature is within a specified range or not; and a control step of controlling, when determining in the determining step that the temperature difference exceeds the specified range, an operation state of a temperature adjusting element for adjusting the detected ambient temperature so as to get approximate to the target setting temperature, wherein the detected ambient temperature when detecting the subject substance is adjusted, and the monitoring method may further include a calculation step of calculating, when determining in the determining step that the temperature difference between the acquired temperature and the target setting temperature is within the specified range, numerical value information on the subject substance on the basis of an electric signal generated by the electrochemical sensor. Further, the monitoring method according to the present invention can further include a result displaying step of displaying a calculated result in the calculation step on a result display unit.

Furthermore, in the monitoring method according to the present invention, the detected ambient temperature may be adjusted so as to reach a standby target setting temperature that is set lower than the target setting temperature when standing by for measuring the subject substance.

Further, in the monitoring method according to the present invention, first numerical value information defined as the numerical value information on the subject substance calculated in the calculation step and second numerical value information defined as the numerical value information on the subject substance measured in a way that uses a body fluid sampled in vitro from an examinee may be acquired, and, if a difference between the first numerical value information and the second numerical value information exceeds a predetermined first threshold value, a setting value of the target setting temperature when measuring the subject substance may be changed.

Still further, in the monitoring method according to the present invention, in the case of adjusting the detected ambient temperature so as to reach the standby target setting temperature when standing by for measuring the subject substance, the first numerical value information and the second numerical value information may be acquired, and, if the difference between the first numerical value information and the second numerical value information exceeds a predetermined second threshold value, the setting value of the standby target setting temperature when standing by for measuring the subject substance may be changed on a low-temperature side.

Yet further, in the monitoring method according to the present invention, with respect to the first numerical value information and the second numerical value information, there may be acquired each of the numerical value information corresponding to first timing after the monitoring device has started the measurement and the numerical value information corresponding to second timing that traces back to just a predetermined period from the first timing. Then, if a difference between the second numerical value information at the first timing and the second numerical value information at the second timing is within a predetermined third threshold value and if a difference between the first numerical value information at the first timing and the first numerical value information at the second timing exceeds a predetermined fourth threshold value, the setting value of the target setting temperature when measuring the subject substance may be changed. Moreover, in the monitoring method according to the present invention, in the case of adjusting the detected ambient temperature when standing by for measuring the subject substance so as to reach the standby target setting temperature, if an elapse period reaching the first timing since the start of the measurement exceeds a predetermined reference period, the setting value of the standby target setting temperature when standing by for measuring the subject substance may be changed on the low-temperature side.

Moreover, a monitoring system according to the present invention, which measures numerical value information on a subject substance in a body fluid, can include: a monitoring device having an electrochemical sensor including a sensor unit for detecting the subject substance which is used in the way of being embedded subcutaneously and generating an electric signal correlating to the numerical value information on the subject substance, a sensor control unit for controlling the electrochemical sensor and calculating the numerical value information on the subject substance on the basis of the electric signal generated by the electrochemical sensor, and a temperature control unit which adjusts the detected ambient temperature defined as a temperature ambient to the sensor unit so as to reach a target setting temperature when measuring the subject substance; and a result display device for obtaining a calculated result of the sensor control unit and displaying the calculated result.

In the monitoring system, the monitoring device can be attached to the examinee. Moreover, the monitoring system can further include a temperature sensor which measures the temperature correlating to the detected ambient temperature and a temperature adjusting element which adjusts the detected ambient temperature. Then, the temperature control unit can control an operation state of the temperature adjusting element on the basis of the temperature measured by the temperature sensor.

Further, each of the temperature sensor, the temperature adjusting element and the temperature control unit may be disposed in a housing accommodating the sensor control unit or in the electrochemical sensor. As a matter of course, each of the temperature sensor, the temperature adjusting element and the temperature control unit may also be disposed in at least any one of the housing accommodating the sensor control unit, the electrochemical sensor and the housing provided with the result display device.

Moreover, in the monitoring system, the temperature control unit may adjust the detected ambient temperature when standing by for measuring the subject substance so as to reach the standby target setting temperature set lower than the target setting temperature.

Further, in the monitoring system, the temperature control unit may acquire first numerical value information defined as the numerical value information on the subject substance calculated by the sensor control unit and second numerical value information defined as the numerical value information on the subject substance measured by a second monitoring device in a way that uses a body fluid sampled in vitro from an examinee, and may change, if a difference between the first numerical value information and the second numerical value information exceeds a predetermined first threshold value, a setting value of the target setting temperature when measuring the subject substance.

Moreover, in the monitoring system, the temperature control unit, in the case of adjusting the detected ambient temperature so as to reach the standby target setting temperature when standing by for measuring the subject substance, may acquire the first numerical value information and the second numerical value information, and may change, if the difference between the first numerical value information and the second numerical value information exceeds a predetermined second threshold value, the setting value of the standby target setting temperature, on a low-temperature side, when standing by for measuring the subject substance.

Furthermore, in the monitoring system, the temperature control unit may acquire, with respect to the first numerical value information and the second numerical value information, each of the numerical value information corresponding to first timing after the monitoring device has started the measurement and the numerical value information corresponding to second timing that traces back to just a predetermined period from the first timing. Then, the temperature control unit may change, if a difference between the second numerical value information at the first timing and the second numerical value information at the second timing is within a predetermined third threshold value and if a difference between the first numerical value information at the first timing and the first numerical value information at the second timing exceeds a predetermined fourth threshold value, the setting value of the target setting temperature when measuring the subject substance.

Further, in the monitoring system, the temperature control unit may change, in the case of adjusting the detected ambient temperature so as to reach the standby target setting temperature when standing by for measuring the subject substance and if an elapse period reaching the first timing since the start of the measurement exceeds a predetermined reference period, the setting value of the standby target setting temperature, on the low-temperature side, when standing by for measuring the subject substance.

Further, a program according to the present invention makes a computer for measuring numerical value information on a subject substance by use of an electrochemical sensor having a sensor unit, for detecting the subject substance in a body fluid, disposed in the way of being embedded subcutaneously, the program making the computer execute: a temperature acquiring step of acquiring a measurement result of a temperature sensor which measures a temperature correlating to the detected ambient temperature defined as the temperature ambient to the sensor unit; a determining step of comparing the acquired temperature acquired in the temperature acquiring step with a target setting temperature and determining whether a temperature difference between the acquired temperature and the target setting temperature is within a specified range or not; and a control step of controlling, when determining in the determining step that the temperature difference exceeds the specified range, an operation state of a temperature adjusting element for adjusting the detected ambient temperature so as to get approximate to the target setting temperature. The computer is control computer for controlling any one of the monitoring device or the monitoring system described above.

The program according to the present invention can further make the computer execute a calculation step of calculating, when determining in the determining step that the temperature difference is within the specified range, numerical value information on the subject substance on the basis of an electric signal generated by the electrochemical sensor. Further, the program according to the present invention can further make the computer execute a result displaying step of displaying a calculated result in the calculation step on a result display unit.

Moreover, the program according to the present invention can further make the computer adjust the detected ambient temperature so as to reach a standby target setting temperature that is set lower than the target setting temperature when standing by for measuring the subject substance.

Further, the program according to the present invention can further make the computer acquire first numerical value information defined as the numerical value information on the subject substance calculated in the calculation step and second numerical value information defined as the numerical value information on the subject substance measured in a way that uses a body fluid sampled in vitro from an examinee, and change, if a difference between the first numerical value information and the second numerical value information exceeds a predetermined first threshold value, a setting value of the target setting temperature when measuring the subject substance.

Furthermore, the program according to the present invention can further make the computer, in the case of adjusting the detected ambient temperature so as to reach the standby target setting temperature when standing by for measuring the subject substance, acquire the first numerical value information and the second numerical value information, and change, if the difference between the first numerical value information and the second numerical value information exceeds a predetermined second threshold value, the setting value of the standby target setting temperature when standing by for measuring the subject substance on a low-temperature side.

Moreover, the program according to the present invention can further make the computer, with respect to the first numerical value information and the second numerical value information, acquire each of the numerical value information corresponding to first timing after the monitoring device has started the measurement and the numerical value information corresponding to second timing that traces back to just a predetermined period from the first timing, and, if a difference between the second numerical value information at the first timing and the second numerical value information at the second timing is within a predetermined third threshold value and if a difference between the first numerical value information at the first timing and the first numerical value information at the second timing exceeds a predetermined fourth threshold value, change the setting value of the target setting temperature when measuring the subject substance.

Moreover, the program according to the present invention can further make the computer, in the case of adjusting the detected ambient temperature when standing by for measuring the subject substance so as to reach the standby target setting temperature, if an elapse period reaching the first timing since the start of the measurement exceeds a predetermined reference period, change the setting value of the standby target setting temperature when standing by for measuring the subject substance on the low-temperature side.

Further, the present invention can be grasped as a readable-by-computer recording medium recoded with the program. Moreover, the means for accomplishing the object of the present invention can be combined to the greatest possible degree.

According to the present invention, it is feasible to provide the technology capable of obtaining the measurement result exhibiting the high reliability and the high reproducibility under the state where the change in heat up temperature environment occurs on the occasion of measuring the numerical value information on the subject substance in the body fluid.

DESCRIPTION OF THE PREFERRED EMBODIMENTS

Figure 1:
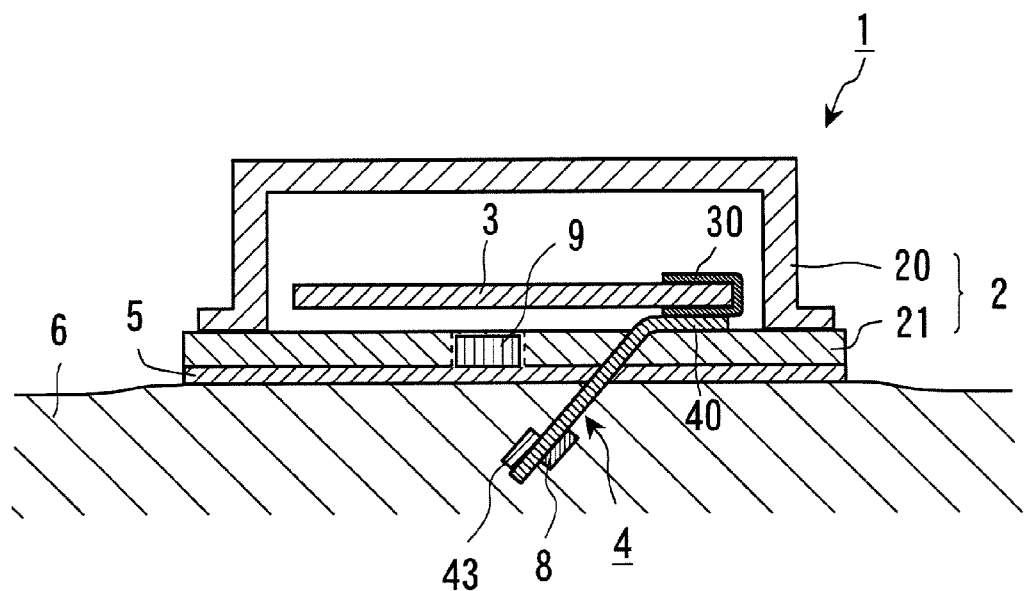
FIG. 1 is a diagram showing an outline of a configuration of a monitoring device in a first working example.

An in-depth description of a mode for carrying out the invention will hereinafter be described on an exemplifying and not-limiting basis with reference to the drawings. The embodiment will discuss a continuous glucose monitoring device attached to an examinee and thus employed by way of one example of a measuring device (monitoring device) according to the present invention. Note that the same components illustrated in the drawings given above are marked with the same reference numerals and symbols. Further, the descriptions of the respective embodiments of the measuring device according to the present invention, which will hereinafter be discussed, serve also as the descriptions of the individual embodiments of a measuring system, a measuring method, a program and a readable-by-computer recording medium recorded with the program.

First Working Example

FIG. 1 is a view illustrating an outline of a configuration of the continuous glucose monitoring (abbreviated to CGM) device (which will hereinafter simply be termed "the monitoring device" or "measuring device") in a first working example. A monitoring device 1 is capable of continuously measuring a glucose concentration in a blood and an interstitial liquid. The monitoring device 1 can be used in the way of being preferably attached to a skin of, e.g., an abdomen region and an arm region of a human body (examinee) but is not limited to this usage mode. This monitoring device 1 includes a housing 2, a control computer 3 and an electrochemical sensor 4.

This electrochemical sensor 4 is a sensor which detects a specified subject substance by making use of electrochemical sensor reaction. The electrochemical sensor 4 in the first working example is classified as a so-called biosensor. The biosensor is a sensor which measures and detects the subject substance in a way that involves using a living organism or a material derived from the living organism as an element of which the subject substance is recognized. The electrochemical sensor 4 in the first working example is employed for measuring the glucose concentration in a body fluid and will therefore be referred to as a "glucose sensor". Furthermore, the glucose in the body fluid corresponds to the "subject substance" according to the present invention, and the glucose concentration can be given as "numerical value information" related to the subject substance according to the present invention.

The housing 2 takes an external shape of the monitoring device 1 and includes a cover 20 and a base plate 21. The cover 20 and the base plate 21, which are fixed to each other, define the housing 2 accommodating the control computer 3. The housing 2 has, it is preferable, a waterproofing property or a water resisting property. In the housing 2 such as this, e.g., at least the cover 20 (and the base plate 21 as the necessity may arise) is composed of a material such as a metal and a polypropylene resin each exhibiting an extremely low water permeability.

The base plate 21 is a portion into which the glucose sensor 4 is inserted, and an end portion (which will hereinafter be termed a [proximal end]) 40 on the proximal side of the glucose sensor 4 is fixed. A bonding film 5 is fixed to the base plate 21. This bonding film 5 is used when fixedly attaching (adhering) the continuous monitoring device 1 to the skin. The bonding film 5 can involve using a double-sided adhesive tape.

The control computer 3 is mounted with electronic components required for predetermined operations (such as applying a voltage, performing temperature control of a detected ambient temperature that will be described later on and calculating the glucose concentration) of the monitoring device 1. This control computer 3 further includes a terminal 30 brought into contact with an electrode 42 (see FIG. 2) of the glucose sensor 4, which will be explained later on. This terminal 30 is employed for acquiring a response current value from the glucose sensor 4 by applying the voltage to the glucose sensor 4.

The glucose sensor 4 serves to acquire the response corresponding to the glucose concentration in the blood and the interstitial liquid. Though the details will be described later on, a tip portion of the glucose sensor 4 is provided with an immobilized enzyme unit 43 as a sensor unit for detecting the glucose in the blood and the interstitial liquid, and this immobilized enzyme unit 43 is employed in the way of being at least implanted subcutaneously. Herein, the glucose sensor 4 is such that the proximal end 40 protrudes from the skin 6 and comes into contact with the terminal 30 of the control computer 3, while a large proportion of other units (including the immobilized enzyme unit 43) thereof are inserted into the skin 6.

Figure 2:
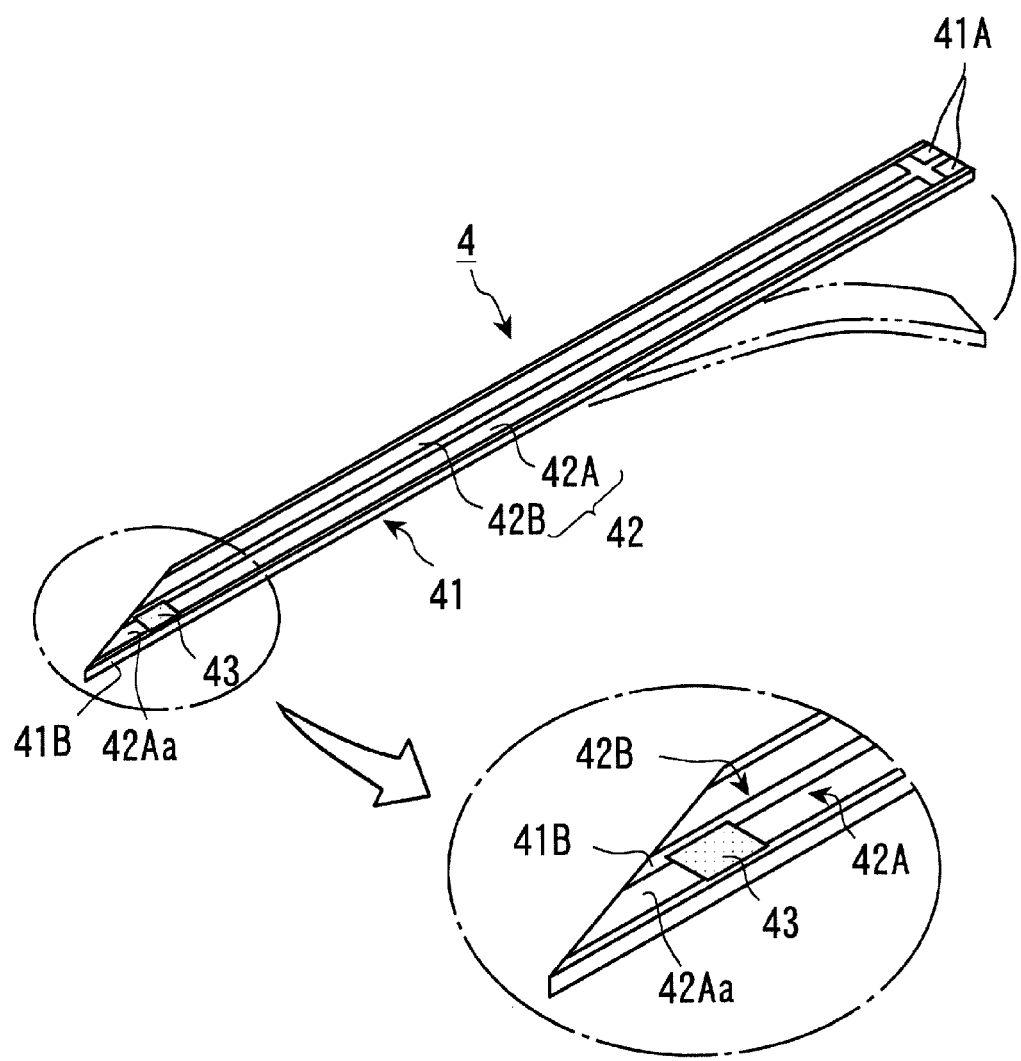
FIG. 2 is a whole perspective view of a glucose sensor together with an enlarged view of a principal portion in the first working example.
Figure 3:
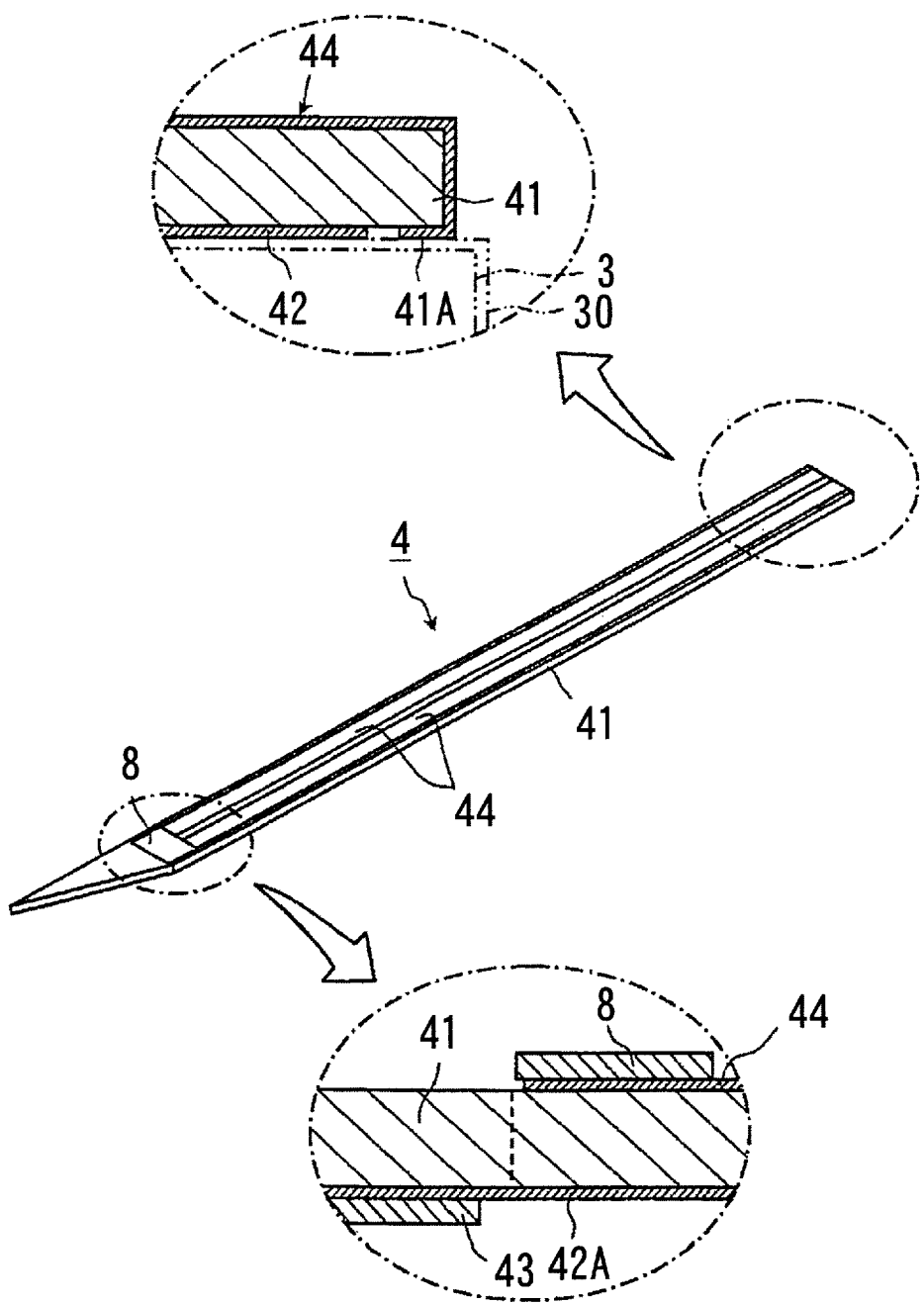
FIG. 3 is a whole perspective view of the glucose sensor together with the enlarged view of the principal portion in the first working example.

FIGS. 2 and 3 are whole perspective views illustrated together with an enlarge view of the principal portion. As illustrated therein, the glucose sensor 4 has a base sheet 41, the electrode 42, the immobilized enzyme unit 43 and a lead wire 44.

The base sheet 41 serves to support the electrode 42 and is formed in a sheet-like shape exhibiting an insulating property and flexibility as well. In the base sheet 41, an end portion 41A exists inside the housing 2, while an end portion 41B is formed in an acute shape. Adoption of the acute structure of the end portion 41B facilitates the insertion of the glucose sensor 4 into the skin 6, thereby enabling a pain of the user (examinee) to be relieved. The end portion 41B is not, however, limited to the specified shape but may take shapes other than the acute shape.

Usable materials for the base sheet 41 may be those having no harmful effect in the human body but the proper insulating property and are exemplified by thermoplastic resins such as polyethyleneterephthalate (PET), polypropylene (PP) and polyethylene (PE) and by thermosetting resins such as a polyimide resin and an epoxy resin.

The electrode 42 is used for applying the voltage to the immobilized enzyme unit 43 and capturing the electrons from the immobilized enzyme unit 43. The electrode 42 includes a working electrode 42A and a counter electrode 42B. The working electrode 42A is an electrode element for transferring and receiving the electrons to and from the glucose. The counter electrode 42B is used for applying the voltage together with the working electrode 42A. The electrode 42 can be produced based on a screen printing technique using, e.g., a carbon ink.

The immobilized enzyme unit 43 serves as a medium for transferring and receiving the electrons between the glucose and the working electrode 42A. This immobilized enzyme unit 43 is formed by immobilizing a glucose oxidoreductase to an end portion 42Aa of the working electrode 42A on one surface (which is herein an upper surface) of the base sheet 41. The glucose oxidoreductase includes an electron-accepting region defined as a region for receiving the electrons derived from a substrate and an electron-donating region defined as a region for donating the electrons derived from the substrate to the working electrode 42A.

The glucose oxidoreductase can involve using glucose oxidase (GOD) and glucose dehydrogenase (GDH). The glucose oxidoreductase involves using preferably the GDH and more preferably cytochrome GDH. The use of the GDH as the glucose oxidoreductase enables the electrons to be taken out (captured) from the glucose without producing any hydrogen peroxide. It is therefore feasible to avoid damaging the glucose and somatic cells of the living organism by the hydrogen peroxide and to realize the glucose sensor 4 that is safer to the human body and exhibits high stability with less of deterioration of the enzyme. A method of immobilizing the glucose oxidoreductase can involve adopting a variety of known methods such as a method of utilizing MPC (2-methacryloxyethyl phosphorylcholine) polymer in which a silane coupling agent is introduced into polymeric gel, high polymer such as polyacrylamide and phosphor and phospholipids polymer, or a protein membrane.

The lead wire 44 serves to transmit items of information measured by a temperature sensor 8 to the control computer 3. A large part of this lead wire 44 is formed on the undersurface (i.e., the surface formed with none of the immobilized enzyme unit 43) of the base sheet 41 of the glucose sensor 4. One end of the lead wire 44 comes into contact with the temperature sensor 8, while the other end is exposed from the upper surface of the base sheet 41 of the glucose sensor 4.

The temperature sensor 8 is a sensor for measuring a detected ambient temperature THs defined as a temperature ambient to the immobilized enzyme unit 43 when the glucose sensor 4 detects the subject substance, i.e., the glucose. This temperature sensor 8 is provided in a position corresponding to the immobilized enzyme unit 43 on the undersurface of the base plate 41 of the glucose sensor 4 in a way that enables the measurement of the temperature ambient to the immobilized enzyme unit 43 of the glucose sensor 4, i.e., enables the measurement of a subcutaneous temperature of the human body (examinee). The temperature sensor 8 is brought into contact with the terminal 30 of the control computer 3 at the end portion 44A via the lead wire 44. The temperature sensor 8 can involve using a variety of known sensors in addition to, e.g., a thermistor.

Figure 4:
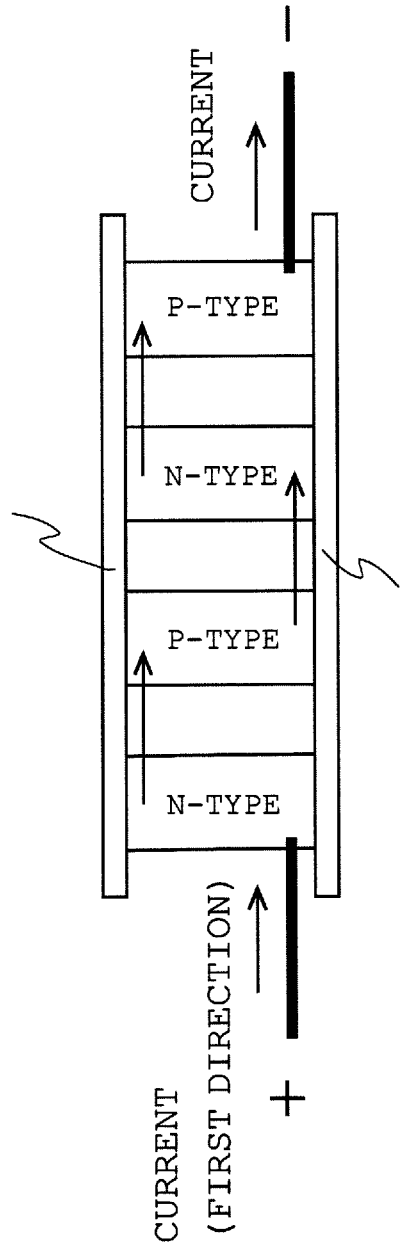
FIG. 4 is an explanatory conceptual diagram of a Peltier device in the first working example.

Further, as illustrated in FIG. 1, the monitoring device 1 includes a Peltier element (Peltier device) 9 classified as one type of thermoelectric transducers. The Peltier device 9 in the first working example is a temperature control device for controlling the detected ambient temperature THs as will be explained later on. FIG. 4 is an explanatory conceptual diagram of the Peltier device in the first working example. As in the conceptual diagram illustrated therein, the Peltier device 9 has a closed circuit formed by establishing a P-N junction of N- and P-type semiconductors and is configured to make switchable a polarity of an electric current flowing to the closed circuit. Herein, one junction surface of the N- and P-type semiconductors is referred to as a "first heat exchange surface 9A", and the other junction surface is referred to as a "second heat exchange surface 9B". Herein, the Peltier device 9 is disposed in such a position that the second heat exchange surface 9B faces the skin side of the examinee, i.e., the [second heat exchange surface 9B] is closer to the skin than the first heat exchange surface 9A. Further, in the first working example, as illustrated in FIG. 1, a notched portion (a recessed portion or a cavity) is formed in the base plate 21, and the Peltier device 9 is set in this notched portion. This contrivance intends to efficiently transmit, down to a subcutaneous tissue, a heat up temperature due to a heat radiation (exothermic) phenomenon or a cool down temperature due to an endothermal phenomenon from the second heat exchange surface 9B.

In the thus-disposed Peltier device 9, when the electric current flows to the P-N junction thereof, the endothermal phenomenon occurs at the N→P junction, while the heat radiation phenomenon occurs at the P→N junction. In this drawing, a direction in which the electric current flows in the illustrated arrowhead (→) direction is set as a "first direction", and a reversed direction is set as a "second direction".

Herein, as illustrated in FIG. 4, when the electric current flows in the first direction, the endothermal phenomenon occurs from the first heat exchange surface 9A, and the exothermic phenomenon occurs from the second heat exchange surface 9B. Namely, in this case, the heat absorbed from on the side of the first heat exchange surface 9A is radiated on the side of the second heat exchange surface 9B, thereby heating the peripheral area of the second heat exchange surface 9B. Further, the periphery of the first heat exchange surface 9A is cooled off by the endothermal action. On the other hand, in the case of inverting the polarity of the electric current and causing the electric current to flow in the second direction, the endothermal phenomenon occurs from the second heat exchange surface 9B, while the exothermic phenomenon occurs from the first heat exchange surface 9A. Accordingly, in this case, it follows that the periphery of the second heat exchange surface 9B is cooled off, while the periphery of the first heat exchange surface 9A is heated up.

In the first working example, the second heat exchange surface 9B of the Peltier device 9 faces the skin side of the examinee, and hence the skin surface is heated by flowing the electric current in the first direction. Then, the heat up temperature transmitted to the subcutaneous tissue, whereby the temperature ambient to the immobilized enzyme unit 43 rises. On the other hand, the skin surface is cooled down this time by flowing the electric current in the second direction while switching over the polarity of the electric current, and the cool down temperature is transmitted to the subcutaneous tissue, whereby the temperature ambient to the immobilized enzyme unit 43 descends. Thus, in the first working example, it is feasible to preferably control the temperature ambient to the immobilized enzyme unit 43.

Figure 5:
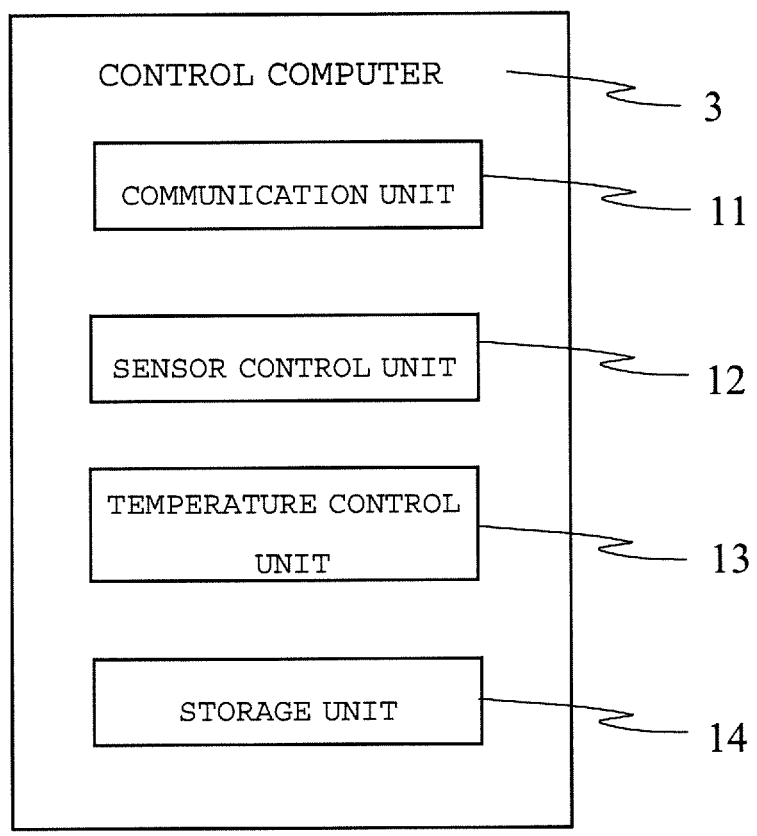
FIG. 5 is a block diagram of functions realized by a control computer of the monitoring device in the first working example.

Next, each of functions provided in the monitoring device 1 will be described. FIG. 5 is a block diagram of the functions realized by the control computer 3 of the monitoring device 1 in the first working example. The control computer 3 in the first working example is a computer including a general purpose or dedicated processor which controls the respective function units by processing instructions and data, a ROM (Read Only Memory) stored with a variety of control programs, a RAM (Random Access Memory) on which the control programs are deployed, a hard disk (Hard Disk) stored with various items of data used by the monitoring device 1 as the necessity may arise, and so on. The processor interprets and executes the control programs deployed on the RAM. These configurations may, including the processor, be individually provided in the respective function units and may also be shared with the respective function units.

A sensor control unit 12 realizes a function of controlling the variety of operations such as setting voltage application timing, setting an applied voltage value, sampling the response current, calculating the glucose concentration and performing the communications with external information processing terminals according tote necessity. The temperature control unit 13 functions in cooperation with the temperature sensor 8 and the Peltier device 9 in order to control the temperature so that the detected ambient temperature THs becomes a target setting temperature THtg when the glucose sensor 4 detects the subject substance. The detected ambient temperature THs is the temperature ambient to the immobilized enzyme unit 43. Further, the target setting temperature THtg will be described later on.

A communication unit 11 realizes the function of performing the data communications between the monitoring device and the external information processing terminals. This communication unit 11 has a transmitting unit and includes a receiving unit as the case may arise. The data communications can involve utilizing a wireless communication means (IrDA (Infrared Data Association) using infrared rays or Bluetooth employing a frequency band of 2.4 GHz). As a matter of course, the wired data communications may also be conducted via a cable between the communication unit 11 of the monitoring device 1 and the external information processing terminals.

The external information processing terminals can be exemplified such as a display unit (a result display unit) for displaying a result of measuring the glucose concentration, an insulin injecting device (e.g., an insulin pump) for dosing the insulin to the human body, a simplified type blood glucose level measuring device, an external personal computer and an alarm device. The alarm device is a device which informs a patient of individual states showing that the examinee comes to glucopenia or hyperglycemia or has a symptom of becoming the glucopenia or the hyperglycemia on the basis of the data given from the monitoring device 1.

The data communications between the monitoring device 1 and the insulin injecting device are performed by transmitting, e.g., the glucose concentration measured result given from the monitoring device 1 to the insulin injecting device. This scheme enables an insulin dosage, which should be given to the human body, to be controlled based on the measured data sent transmitted from the monitoring device 1.

The data communications between the monitoring device 1 and the simplified type blood glucose level measuring device are carried out by transmitting, e.g., a blood glucose level measured result given from the simplified type blood glucose level measuring device to the monitoring device 1. With this scheme, when the measured result of the monitoring device 1 is compared with the measured result of the simplified type blood glucose level measuring device and if a gap between these measured results is equal to or larger than a fixed value, the monitoring device 1 may be calibrated. The raw data (response current) measured by the monitoring device 1 may also be transmitted to the simplified type blood glucose level measuring device.

The data communications between the monitoring device 1 and the display unit are performed by transmitting, e.g., the glucose concentration measured result given from the monitoring device 1 to the display unit. Note that the display unit may be used in a portable (attachable) mode for the examinee (which can be exemplified by a wrist watch type display machine and a portable type display machine attached to the skin surface in the vicinity of the monitoring device 1) and may also be used otherwise. Further, the display unit can be configured in such a mode that the display unit is formed integrally with the monitoring device 1 in the way of being included as a part of the monitoring device 1. Thus, the display unit, to which the measured result of the monitoring device 1 is transmitted, displays this measured result, thereby enabling the user (examinee) to easily recognize and grasp the present blood glucose level.

The data communications between the monitoring device 1 and the personal computer are performed by transmitting, e.g., the blood glucose level measured result and the raw data (response current) to the personal computer. This scheme enables a transition of the glucose concentration to be monitored on the personal computer.

The storage unit 14 is a unit stored with programs and data required for the variety of calculations (e.g., data about a working curve and data about a voltage application pattern). This storage unit 14 may also be a unit capable of storing the response current value and the calculated glucose concentration given from the glucose sensor 4.

Next, an in-depth description of the temperature control unit 13 will be made. Herein, the monitoring device 1 according to the first working example detects the glucose in the body fluid by making use of the enzyme reaction of the enzyme retained by the immobilized enzyme unit 43 in the glucose sensor 4. Then, a continuous operation period of the monitoring device 1 covers, it is desirable, preferably several days and more preferably one week through a few weeks.

Accordingly, during the operation period of the monitoring device 1, it follows that the external heat up temperature environment around the examinee momentarily changes. Namely, factors for fluctuations of the subcutaneous temperature are a change in living environment (e.g., an outdoor air temperature) and a case of engaging in activities in daily living typified by bathing, taking a shower and taking excises.

In this connection, the glucose oxidoreductase in the immobilized enzyme unit 43 fluctuates in enzyme activity due to the reaction temperature, and hence it is necessary to cancel influence of the change in heat up temperature environment around the examinee. Such being the case, the monitoring device 1, when the glucose sensor 4 detects the glucose, conducts temperature adjustment control for adjusting the temperature so that the detected ambient temperature THs defined as the temperature ambient to the immobilized enzyme unit 43 reaches the target setting temperature THtg.

The target setting temperature THtg is a target temperature set when adjusting the detected ambient temperature THs under the temperature adjustment control and is, as far as the glucose concentration is measured in a status where the detected ambient temperature THs is kept in the vicinity of this target temperature, a temperature considered not to affect the measured result even when the heat up temperature environment fluctuates. In the first working example, the target setting temperature THtg is preset based on an empirical rule, within a range of, e.g., normal temperature.

The temperature adjustment control is realized by the temperature control unit 13 which controls the operation state of the Peltier device 9 on the basis of the temperature measured by the temperature sensor 8. Herein, the temperature sensor 8 is connected to the temperature control unit 13 via the lead wire 44, and the information measured by the temperature sensor 8 is inputted to the temperature control unit 13 of the control computer 3. Further, the Peltier device 9 is electrically connected to the control computer 3, whereby the temperature control unit 13 controls the operation state of the Peltier device 9.

Figure 6:
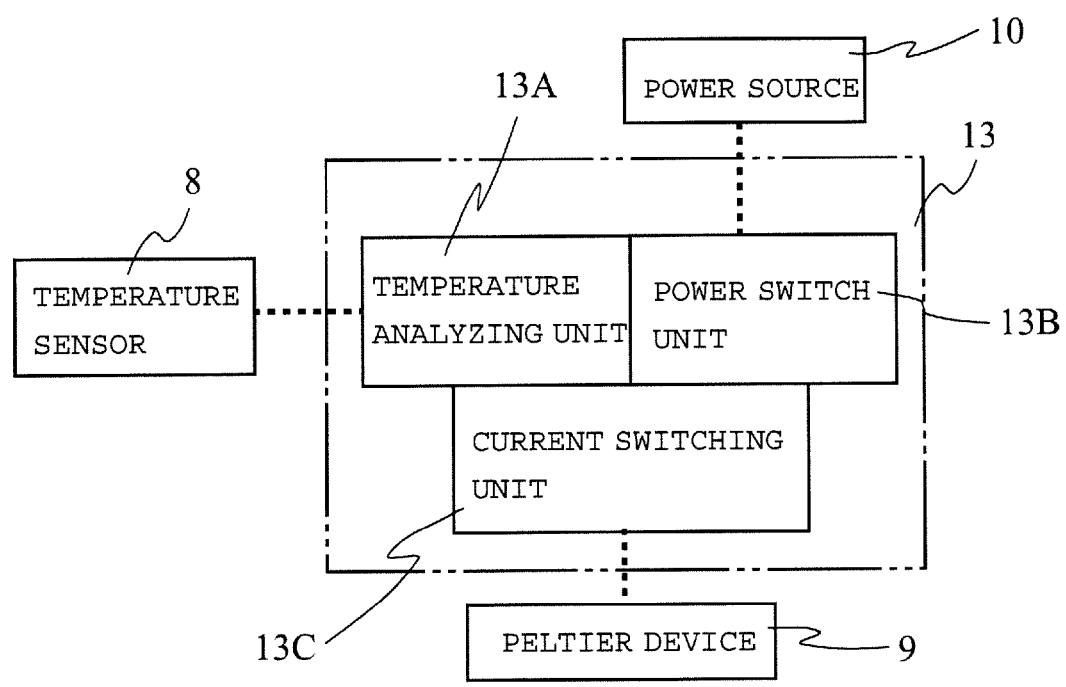
FIG. 6 is a block diagram showing an outline of a configuration of a temperature control unit in the first working example.

Herein, an example of a configuration of the temperature control unit 13 will hereinafter be described with reference to FIG. 6. In the example of the configuration in FIG. 6, the temperature control unit 13 is configured by including a temperature analyzing unit 13A, a power switch unit 13B and a current switching unit 13C. Further, the temperature control unit 13 is supplied with a direct current (DC) from a power source 10. The power source 10 can involve adopting a button battery of which a power voltage is on the order of 1V-3V but is not limited to this type of battery. Moreover, the power source 10 can supply the electric power to other function units (e.g., the sensor control unit 12) of the control computer 3 and the glucose sensor 4.

The power switch unit 13B is an electronic component which switches ON/OFF the electric power supplied to the Peltier device 9. Further, the current switching unit 13C is an electronic component capable of inverting the polarity of the direct current supplied to the Peltier device 9 and switching over the current direction to anyone of the first direction and the second direction. Moreover, the temperature analyzing unit 13A acquires the measured result of the detected ambient temperature THs inputted from the temperature sensor 8 and determines, based on the result of the comparison with the target setting temperature THtg, a content of the control with respect to the Peltier device 9.

Figure 7:
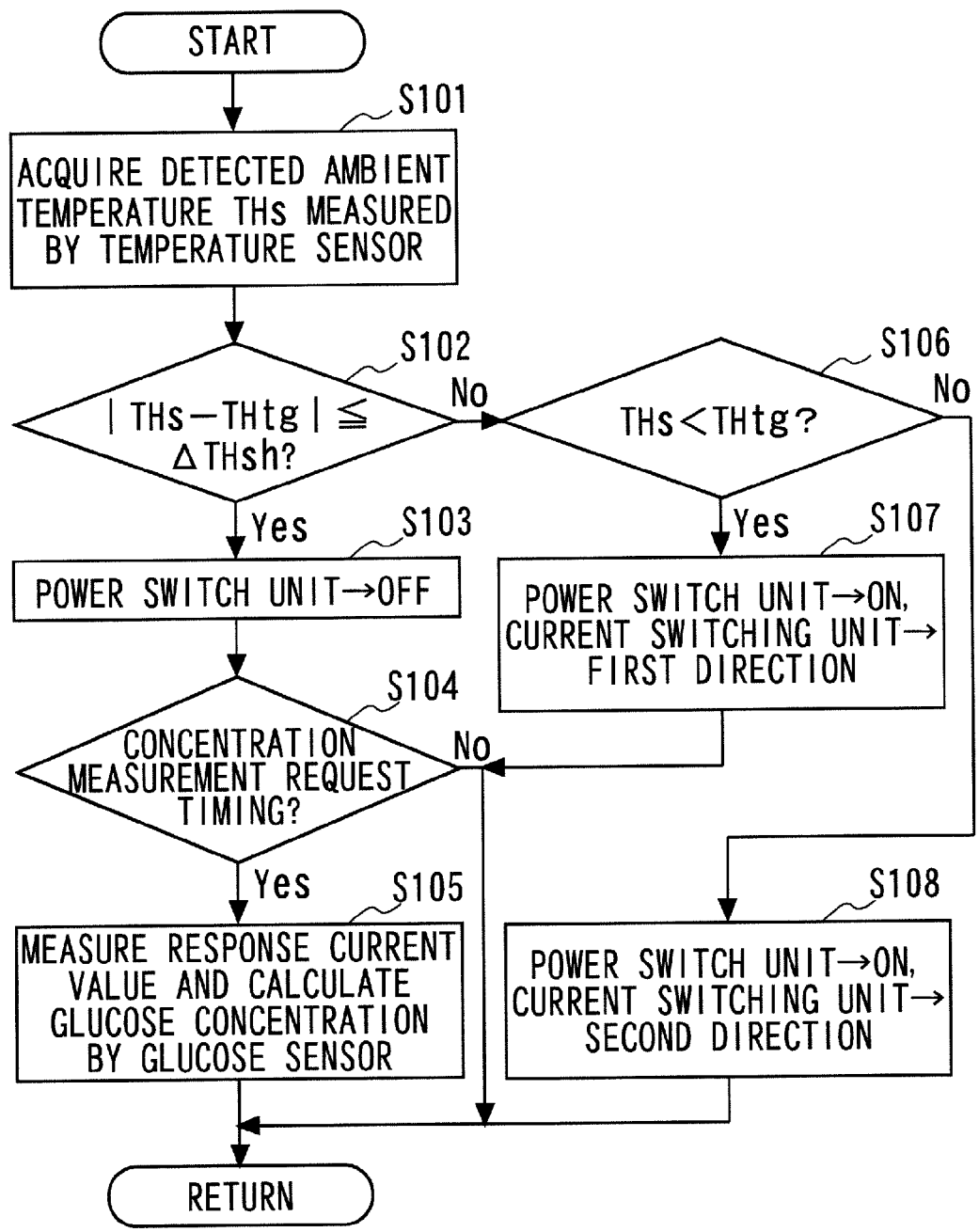
FIG. 7 is a flowchart showing a control routine when the monitoring device measures a glucose concentration in the first working example.

FIG. 7 is a flowchart illustrating a processing flow when the continuous glucose monitoring device measures the glucose concentration. When the power source of the monitoring device 1 is in an ON-state, the control computer 3 deploys, on the RAM, the control program stored in the ROM, and the processor executes the control program at an interval of a fixed period of time, thereby realizing the respective processes in the flowchart. Namely, the individual functions provided in the control computer 3 explained in FIG. 5 are actualized in such a way that the processor of the control computer 3 cooperates with the control program stored in the ROM.

When starting the execution of the control program, to begin with, in step S101, the temperature control unit 13 acquires the detected ambient temperature THs based on an output signal of the temperature sensor 8. Herein, the temperature sensor 8 measures the detected ambient temperature THs at the interval of executing the control program, i.e., at the interval of the predetermined fixed period of time, and the measurement data thereof is inputted to the temperature analyzing unit 13A of the temperature control unit 13. Step S101 in the flowchart corresponds to a temperature acquiring step according to a measurement method of the present invention.

In step S102, the temperature analyzing unit 13A of the temperature control unit 13 compares the acquired detected ambient temperature THs with the target setting temperature THtg. Then, it is determined whether or not an absolute value of a difference between the detected ambient temperature THs and the target setting temperature THtg falls within a range of a specified temperature difference $\Delta$THsh. If determined to be affirmative in this step ($|THs-THtg| \leq \Delta THsh$), the detected ambient temperature THs can be deemed to be coincident with the target setting temperature THtg or to be sufficiently approximate to the target setting temperature THtg. In this case, even when the detected ambient temperature THs is not adjusted more elaborately than this, it is considered that the enzyme activity of the enzyme immobilized by the immobilized enzyme unit 43 has no variation as affected by the external ambient temperature. Namely, if the glucose concentration is measured in this state, it is determined that there is no possibility that a measurement error might occur due to the fluctuations of the external ambient temperature, and the operation proceeds to step S103.

In step S103, when the power switch unit 13B is kept ON, the power switch unit 13B is switched OFF and, as a result, the power supply to the Peltier device 9 is stopped. Namely, the operation of the Peltier device 9 is stopped. Note that the power switch unit 13B remains OFF from the beginning, the operation may proceed directly to next step S104.

In step S104, it is determined whether the should-be-measured timing (measurement request timing) of the glucose concentration is reached at the present or not. A contrivance in the monitoring device 1 according to the first working example is that the glucose concentration is automatically measured, e.g., at the preset interval (e.g., at such a frequency that the measurement may be conducted once for several minutes) or at the predetermined timing. As a matter of course, also when the user (examinee) gives a manual measurement request (such as pressing a measurement start button), the glucose concentration can be measured separately. The timing is determined to be the measurement timing of the glucose concentration in this step, in which case the operation proceeds to step S105, but, whereas if not so, the execution of the present control program is temporarily terminated.

In step S105, the sensor control unit 12 applies the voltage to between the electrodes 42 (between the working electrode 42A and the counter electrode 42B) of the glucose sensor 4.

As a result, the glucose in the body fluid is reduced (the electrons are captured) by the oxidoreductase of the immobilized enzyme unit 43, and the electrons thereof are supplied to the working electrode via an electron supplying region. Then, a quantity of the electrons supplied to the working electrode 42A is measured as a response current value. Subsequently, the glucose sensor 4 generates an electric signal which indicates the response current value when the voltage is applied, and the electric signal is output to the sensor control unit 12. The electric signal indicating the response current value is an electric signal having a correlation with the concentration of the glucose defined as the subject substance. The sensor control unit 12 receiving the electric signal inputted from the glucose sensor 4 calculates, based on the response current value, the glucose concentration (blood glucose level). When calculating the glucose concentration herein, there is no necessity for making the temperature correction corresponding to the external ambient temperature. As discussed above, in the present step, the sensor control unit 12 controlling the glucose sensor 4 calculates the glucose concentration on the basis of the electric signal generated by the glucose sensor 4. Then, step S105 in this flowchart corresponds to a calculating step according to the measurement method of the present invention.

Furthermore, the communication unit 11 outputs the calculated result of the glucose concentration to the display unit, and the display unit displays the acquired measured result (calculated result) of the glucose concentration. Through this display, the examinee (user) is informed of the measured result of the glucose concentration. Moreover, the calculated result of the glucose concentration may also be transmitted to other external information terminals. Upon finishing the process in this step, the execution of the control program is temporarily terminated.

Given next is a description of a case in which the absolute value of the difference between the detected ambient temperature THs and the target setting temperature THtg does not fall within the range of the specified temperature difference $\Delta$THsh ($|THs-THtg| > \Delta THsh$) in step S102. This case is, it follows, applicable to that the detected ambient temperature THs is lower to some degree than the target setting temperature THtg or that THs is conversely higher to some degree than the target setting temperature THtg.

Then, in this case, the operation proceeds to step S106, in which the temperature control unit 13 determines whether or not the detected ambient temperature THs is lower than the target setting temperature THtg. Herein, if determined to be affirmative (THs<THtg), the temperature control unit 13 determines it necessary to increase the detected ambient temperature THs, and the operation proceeds to step S107. Whereas if determined to be negative, the temperature control unit 13 determines it necessary to decrease the detected ambient temperature THs, and the operation proceeds to step S108. Herein, the process in step S102 corresponds to a determining step according to the measurement method of the present invention.

In step S107, the temperature control unit 13, when the power switch unit 13B is in the OFF state, switches OFF this unit 13B, and simultaneously controls the current switching unit 13C so that the direction of the direct current supplied to the Peltier device 9 is switched over to the first direction. The skin in the vicinity of the Peltier device 9 is thereby heated. Herein, the immobilized enzyme unit 43 of the glucose sensor 4 is normally embedded to a depth on the order of several millimeters (mm) at the deepest from the skin, and the Peltier device 9 heats up the skin surface, whereby the heat thereof can be sufficiently propagated to the region in the vicinity of the immobilized enzyme unit 43. As a result, the detected ambient temperature THs can be raised up to the target setting temperature THtg, preferably.

Note that herein the number of the semiconductors configuring the Peltier device 9, a magnitude of the value of the electric current to be supplied and, for others, a physical property value related to the Peltier device 9 are designed within a proper range so as not to excessively increase or decrease a changing speed (which is herein a rising speed) of the detected ambient temperature THs. This is similarly applied to the case of supplying the electric current in the second direction to the Peltier device 9 and decreasing the detected ambient temperature THs. Upon finishing the process in this step, the execution of the control program is temporarily terminated.

In step S108, the temperature control unit 13, when the power switch unit 13B is in the OFF state, switches ON this unit 13B, and simultaneously controls the current switching unit 13C so that the direction of the direct current supplied to the Peltier device 9 is switched over to the second direction. The endothermal phenomenon thereby occurs from the skin in the vicinity of the Peltier device 9, thus cooling the skin surface. Then, this cool down temperature is sufficiently propagated to the region vicinal to the immobilized enzyme unit 43, and hence the detected ambient temperature THs can be preferably lowered down to the target setting temperature THtg. Upon finishing the process in this step, the execution of the control program is temporarily terminated. The processes in steps S107 and S108 in the present flowchart correspond to a control step according to the measurement method of the present invention.

The control program described above is executed iteratively on the per-fixed-time basis. Therefore, for example, the process related to step S107 or S108 continues till the affirmative determination is made in step S102 from next time onward. Hence, according to the temperature adjustment control in the first working example, after maintaining such a temperature that the detected ambient temperature THs gets coincident with the target setting temperature THtg or a temperature that is sufficiently approximate to the target setting temperature THtg, e.g., the temperature deemed to be equal to the target setting temperature THtg, the glucose concentration can be measured. Further, as for the glucose concentration measurement method according to the first working example, the temperature is adjusted so that the detected ambient temperature THs given when detecting the glucose defined as the subject substance reaches the target setting temperature THtg.

According to the temperature adjustment control in the first working example, even under the state where the external heat up temperature environment around the examinee changes, on the occasion of measuring the glucose concentration, it is feasible to preferably restrain the change in heat up temperature environment from adversely affecting the measured result of the subject substance. Moreover, according to the present control, the electric signal generated by the glucose sensor 4 does not need undergoing the temperature-correction corresponding to the heat up temperature environment at that point of time. It is therefore possible to amply enhance reliability and reproducibility with respect to the measured result of the monitoring device 1.

It should be noted that the present invention can be grasped as a control program for making the control computer 3 execute the respective processes explained in FIG. 7, i.e., a program for realizing the respective functions of the control computer 3 or a readable-by-computer recording medium recorded with this program. These functions can be provided by making the computer read and execute the program on the recording medium. Herein, the readable-by-computer recording medium connotes a recording medium capable of storing information such as data and programs electrically, magnetically, optically, mechanically or by chemical action, which can be read from the computer etc. Among these recording mediums, for example, a flexible disc, a magneto-optic disc, a CD-ROM, a CD-R/W, a DVD, a DAT, an 8 mm tape, a memory card, etc are given as those removable from the computer. Further, a hard disc, a ROM (Read-Only Memory), etc are given as the recording mediums fixed within the computer.

Second Working Example

Figure 8:
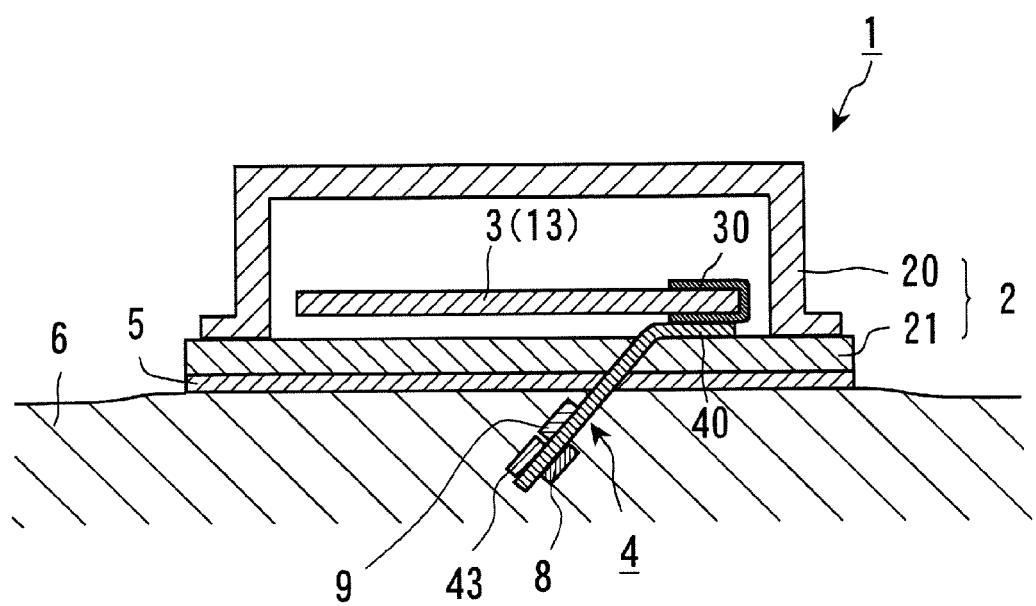
FIG. 8 is an explanatory diagram illustrating positions where a temperature sensor, the Peltier device and a temperature control unit according to a second working example are disposed.

Herein, a second working example will be described with reference to FIG. 8. FIG. 8 is an explanatory diagram for illustrating layout positions of the temperature sensor 8, the Peltier device 9 and the temperature control unit 13 according to the second working example. The second working example is common to the first working example except a point that the layout positions of the respective components are different from those in the first working example. The discussion will be focused on the different point from the already-described working example, and the explanations of the common points are omitted.

In the layout example illustrated in FIG. 1, the temperature control unit 13 and the Peltier device 9 are disposed in the housing 2 which accommodates the control computer 3, and the temperature sensor 8 is disposed in the glucose sensor 4. Note that the housing 2 can be said to be, in other words, the housing 2 which accommodates the sensor control unit 12. In the second working example, the Peltier device 9 is also disposed on the base sheet 41 of the glucose sensor 4. Note that, as illustrated in FIG. 8, the layout positions of the temperature sensor 8 and the temperature control unit 13 are the same as in the example of FIG. 1. A reason why the numeral 3 is attached with the numeral 13 put in parentheses is that the temperature control unit 13 in the second working example is, as already discussed in the first working example, realized by the control computer 3. This is the same in other working examples which follow, unless specified otherwise.

Over the recent years, a small-sized Peltier device formed a few millimeters square (e.g., approximately 1 mm-2 mm square) in size has been commercialized (such as product numbers YKMG, YKMK, YKMA, YKMF manufactured by Yamaha Corp.). Accordingly, for instance, a width of the base sheet 41 of the glucose sensor 4 is set to, e.g., about 5 mm, in which case the Peltier device 9 can be formed sufficiently on the surface of the base sheet 41 by use of the small-sized Peltier device 9 as described above, and this configuration can be preferably embodied. According to this configuration, the region vicinal to the immobilized enzyme unit 43 of the glucose sensor 4 can be directly heated or cooled.

Third Working Example

Figure 9:
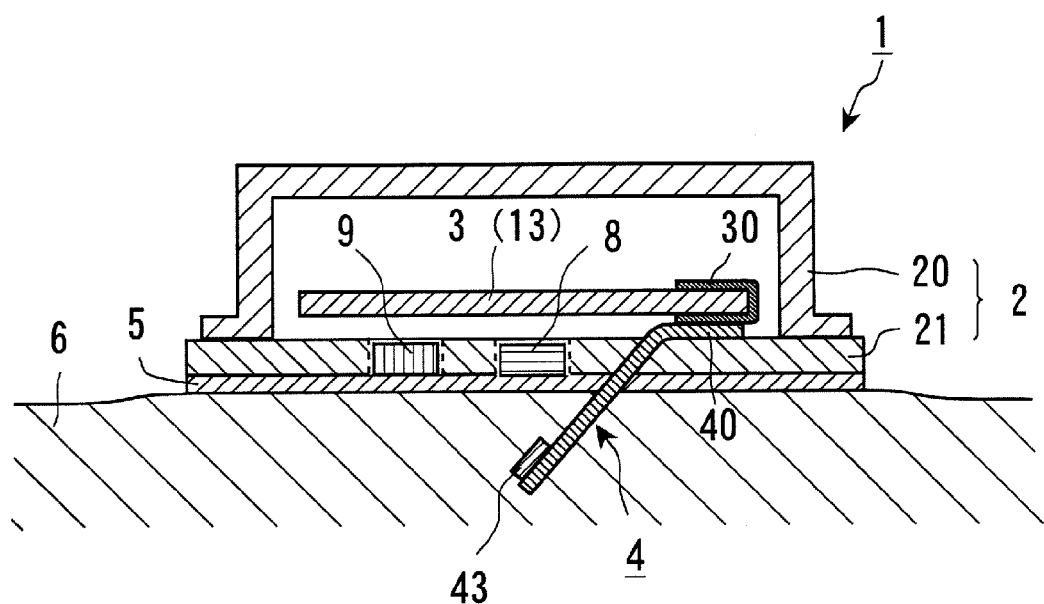
FIG. 9 is an explanatory diagram illustrating the positions where the temperature sensor, the Peltier device and the temperature control unit according to a third working example are disposed.

A third working example will be described with reference to FIG. 9. FIG. 9 is an explanatory diagram for illustrating layout positions of the temperature sensor 8, the Peltier device 9 and the temperature control unit 13 according to the third working example. A different point of the layout positions of the respective components in the third working example from FIG. 1 is that the housing 2 accommodates the temperature sensor 8 in addition to the Peltier device 9. Further, the temperature control unit 13 is the same as in the example illustrated in FIG. 1. In FIG. 9, the temperature sensor 8 is disposed in, e.g., the notched portion (the recessed portion or the cavity) of the base plate 21 in the same way as the Peltier device 9 is.

The temperature sensor 8 in the third working example is disposed not subcutaneously but on the skin surface, and hence the temperature measured by the temperature sensor 8 is substantially coincident with the temperature of the skin surface. The temperature of the skin surface is a temperature which has a correlation with or can be related to the detected ambient temperature THs. Accordingly, in the third working example, the detected ambient temperature THs is estimated based on a positional relation between the position in which the immobilized enzyme unit 43 disposed subcutaneously and the position in which the temperature sensor 8 measures the temperature (the position in which the temperature sensor 8 is disposed) and based on the measurement temperature measured by the temperature sensor 8.

For example, a map is generated, which is stored with the detected ambient temperature THs, the skin surface temperature measured by the temperature sensor 8, a relational formula of a subcutaneous embedding depth of the immobilized enzyme unit 43 and relations therebetween, whereby the detected ambient temperature THs can be estimated by substituting the skin surface temperature and the embedding depth therein. Then, the temperature adjustment control explained in the first working example can be preferably conducted based on the thus-estimated detected ambient temperature THs.

Moreover, in the configuration according to the third working example, the temperature sensor 8 can be disposed on the skin surface. An advantage of this layout is that the temperature sensor 8 does not need embedding subcutaneously, and a size of a portion, embedded subcutaneously, of the base sheet 41 of the glucose sensor 4 can be thereby reduced. As a result, this advantage is useful for relieving a damage to the examinee (user), which is caused when inserting the glucose sensor 4 subcutaneously and for improving facilitation of the insertion.

Figure 10:
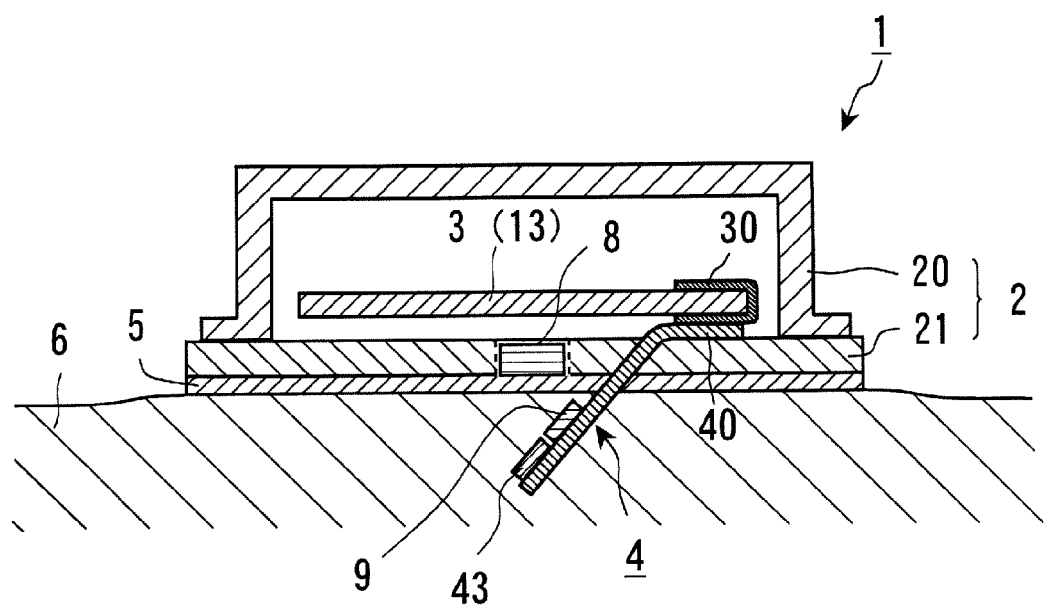
FIG. 10 is an explanatory diagram illustrating the positions where the temperature sensor, the Peltier device and the temperature control unit according to a modified example of the third working example are disposed.

To give a modified example of the third working example incidentally, in the layout example of FIG. 10, the point that the Peltier device 9 is disposed on the base sheet 41 of the glucose sensor 4 is different from the example in FIG. 9, and other points are common.

As exemplified in the first through third working examples, it is feasible to adopt a multiple variation of layout positions of the temperature sensor 8, the Peltier device 9 and the temperature control unit 13 of the monitoring device 1. Further, in each layout example, the housing 2 accommodates the temperature control unit 13, however, any inconvenience may not be caused by disposing the temperature control unit 13 on the base sheet 41 of the glucose sensor 4. Namely, the temperature sensor 8, the Peltier device 9 and the temperature control unit 13 of the monitoring device 1 can be disposed in any one of the housing 2 accommodating the sensor control unit 12 and the glucose sensor 4.

Fourth Working Example

Figure 11:
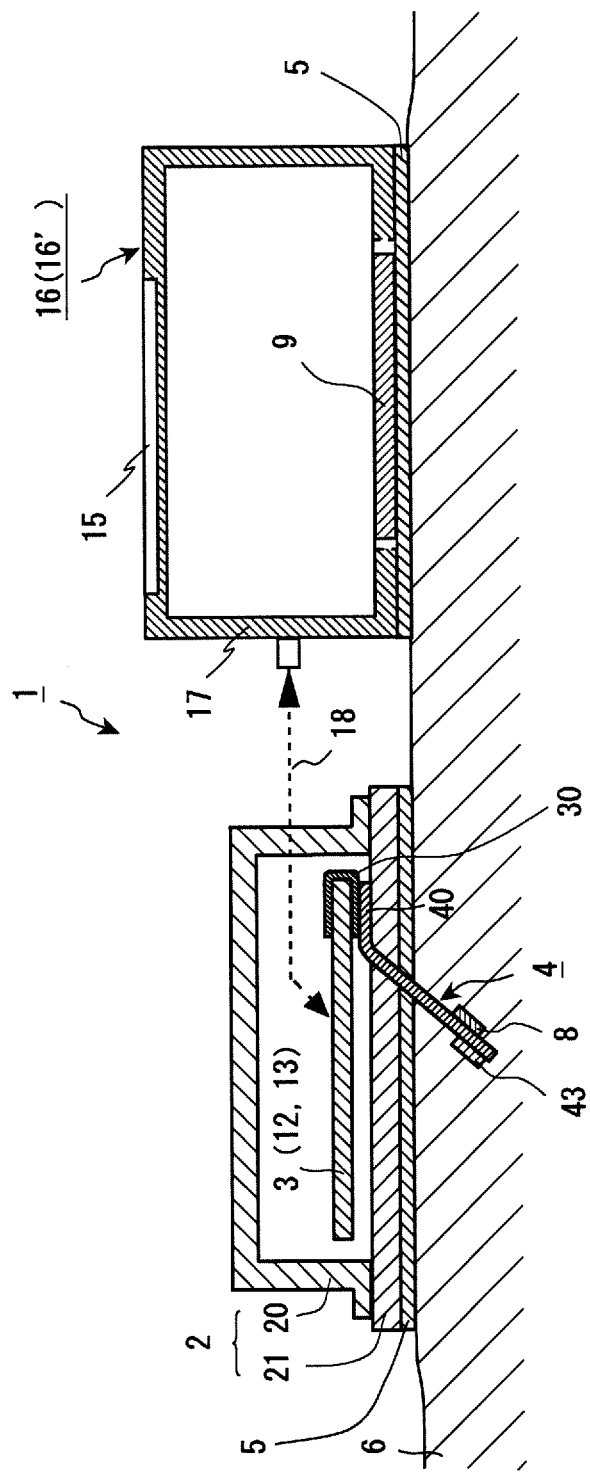
FIG. 11 is a diagram showing an outline of a configuration of the monitoring device according to a fourth working example.

Next, a fourth working example will be described. FIG. 11 is a diagram illustrating an outline of a configuration of the continuous glucose monitoring device (monitoring system) in a fourth working example. The monitoring device 1 in the fourth working example further includes a portable display machine 16 (a result display unit) which acquires the calculated result of the glucose concentration given by the sensor control unit 12 and has a display panel 15 for displaying the calculated result. Namely, the monitoring device 1 can be configured by including the portable display machine 16. A housing 17 of the portable display machine 16 is fixed to the skin by the bonding film 5 in the same way as the housing 2 is fixed. The portable display machine 16 in FIG. 11 performs the wired data communications with the sensor control unit 12 via a cable 18. Herein, the portable display machine 16 can be treated as a portable display machine 16' separated from the monitoring device 1. In this case, the present invention can be also grasped by way of a monitoring system including the monitoring device 1 and the portable display machine 16'. This point is the same with FIGS. 12-15 that will be given later on.

Next, the layout positions of the temperature sensor 8, the Peltier device 9 and the temperature control unit 13 in the fourth working example will be explained. In the layout example depicted in FIG. 11, the temperature sensor 8 is disposed on the base sheet 41 of the glucose sensor 4, the temperature control unit 13 is disposed in the housing 2 accommodating the sensor control unit 12, and the Peltier device 9 is disposed in the housing 17 for the portable display machine 16. In this case, the Peltier device 9 is easy to be disposed at a farther distance from the immobilized enzyme unit 43 of the glucose sensor 4 than in the case of disposing the Peltier device 9 in the housing 2 as illustrated in, e.g., FIG. 1. The housing 17 for the portable display machine 16 in the fourth working example is, however, formed to have a larger projection area on the skin surface than that of the housing 2 accommodating the sensor control unit 12. It is therefore possible to avoid decreasing the efficiency when adjusting the detected ambient temperature THs under the temperature adjustment control described above by increasing the number of semiconductors configuring the Peltier device 9 to such a degree as to get spaced away from the temperature adjustment target immobilized enzyme unit 43.

Figure 12:
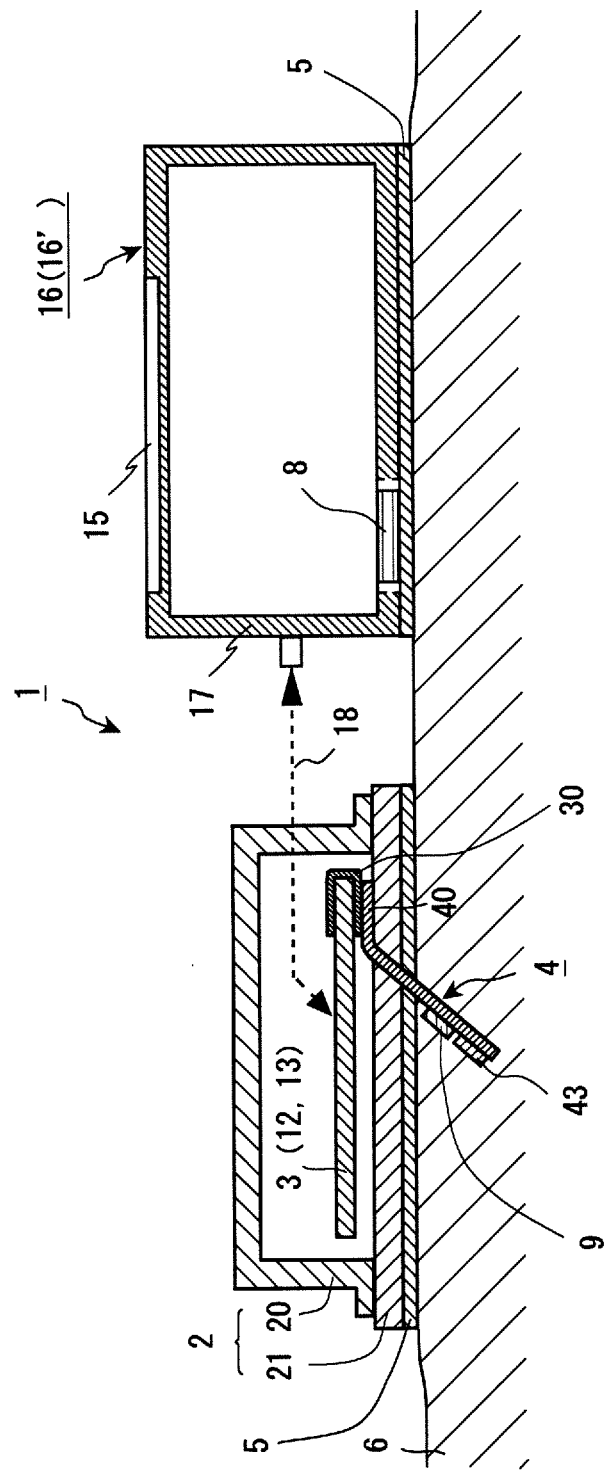
FIG. 12 is an explanatory diagram illustrating the positions where the temperature sensor, the Peltier device and the temperature control unit according to a first modified example of the fourth working example are disposed.

FIGS. 12-15 illustrate the layout examples, different from FIG. 11, of the temperature sensor 8, the Peltier device 9 and the temperature control unit 13. The layout example depicted in FIG. 12 is that the temperature sensor 8 is disposed in the housing 17 for the portable display machine 16, the temperature control unit 13 is disposed in the housing 2 accommodating the sensor control unit 12, and the Peltier device 9 is disposed on the base sheet 41 of the glucose sensor 4. Herein, in the case of disposing the temperature sensor 8 in the housing 17 as illustrated therein, the temperature sensor 8 is easy to be disposed at a still farther distance from the immobilized enzyme unit 43 of the glucose sensor 4 than in the case of the disposition in the housing 2 as in the example of, e.g., FIG. 9. The temperature of the skin surface that is measured by the temperature sensor 8 and the detected ambient temperature THs can be, however, related to each other as described above. Accordingly, the detected ambient temperature THs can be estimated based on the position of the immobilized enzyme unit 43, the layout position of the temperature sensor 8 and the temperature measured by the temperature sensor 8, and the temperature adjustment control can be preferably done based on this estimated result.

Figure 13:
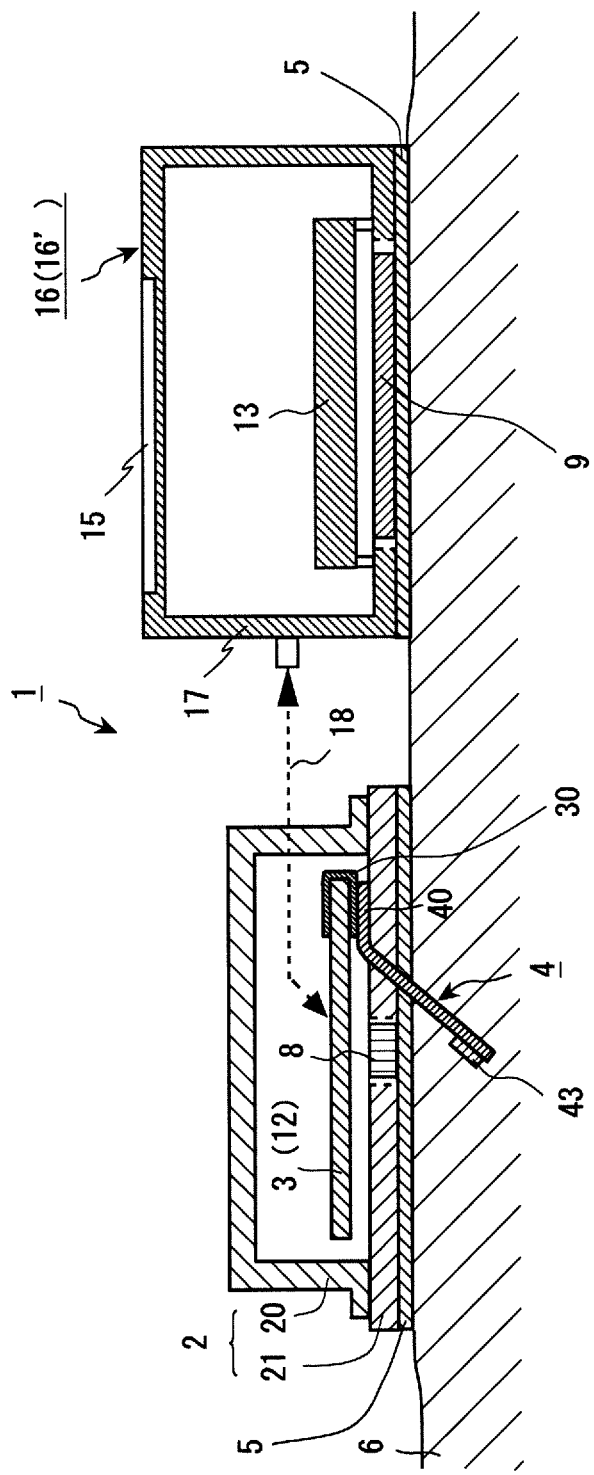
FIG. 13 is an explanatory diagram illustrating the positions where the temperature sensor, the Peltier device and the temperature control unit according to a second modified example of the fourth working example are disposed.
Figure 14:
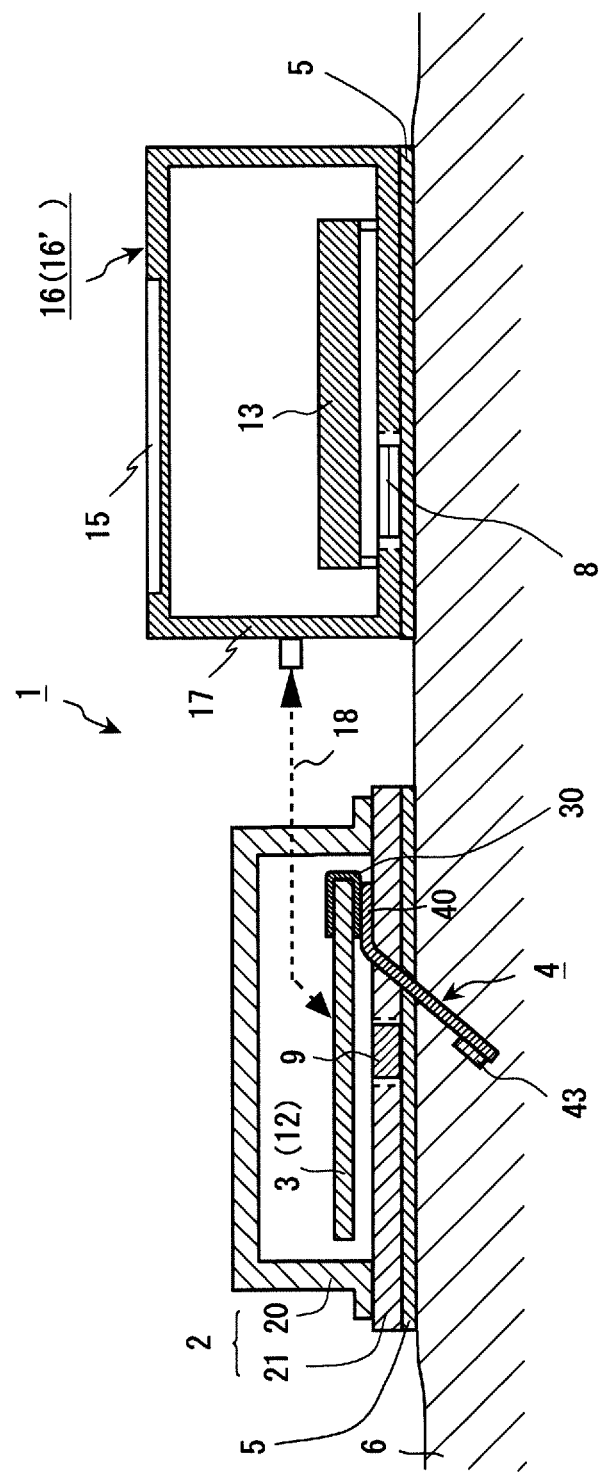
FIG. 14 is an explanatory diagram illustrating the positions where the temperature sensor, the Peltier device and the temperature control unit according to a third modified example of the fourth working example are disposed.
Figure 15:
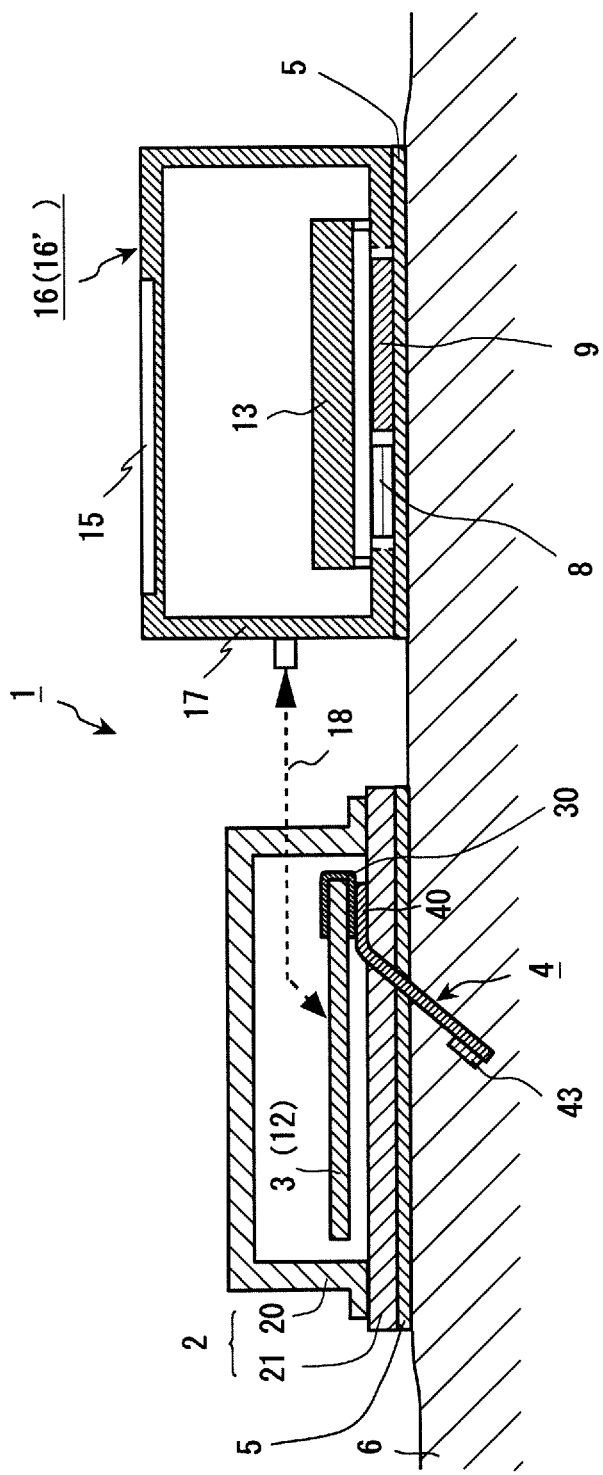
FIG. 15 is an explanatory diagram illustrating the positions where the temperature sensor, the Peltier device and the temperature control unit according to a fourth modified example of the fourth working example are disposed.

Moreover, in the layout example depicted in FIG. 13, the temperature sensor 8 is disposed in the housing 2 accommodating the sensor control unit 12, and the Peltier device 9 and the temperature control unit 13 are disposed in the housing 17 for the portable display machine 16. Further, in the layout example illustrated in FIG. 14, the Peltier device 9 is disposed in the housing 2 accommodating the sensor control unit 12, and the temperature sensor 8 and the temperature control unit 13 are disposed in the housing 17 for the portable display machine 16. Moreover, in the layout example depicted in FIG. 15, all of the temperature sensor 8, the Peltier device 9 and the temperature control unit 13 are disposed in the housing 17 for the portable display machine 16. Incidentally, as illustrated in FIGS. 13-15, a housing 16 accommodates the temperature control unit 13, in which case a second computer (different from the control computer 3) including a CPU, a ROM and a RAM for exhibiting the already-described functions of the temperature control unit 13 are housed inside the housing 16, whereby the second computer can realize the temperature control unit 13.

As exemplified in the fourth working example and the modified example thereof, the layout positions of the temperature sensor 8, the Peltier device 9 and the temperature control unit 13 of the monitoring device 1 can involve adopting the multiple variations. Further, the layout examples of the respective components are not limited to the examples in FIGS. 11-15, and any inconvenience may not be caused by disposing, e.g., the temperature control unit 13 on the base sheet 41 of the glucose sensor 4. Then, each of the temperature sensor 8, the Peltier device 9 and the temperature control unit 13 of the monitoring device 1 can be disposed in any one of the housing 2 accommodating the sensor control unit 12 and the glucose sensor 4 and the housing 17 provided with the portable display machine 16.

Fifth Working Example

Figure 16:
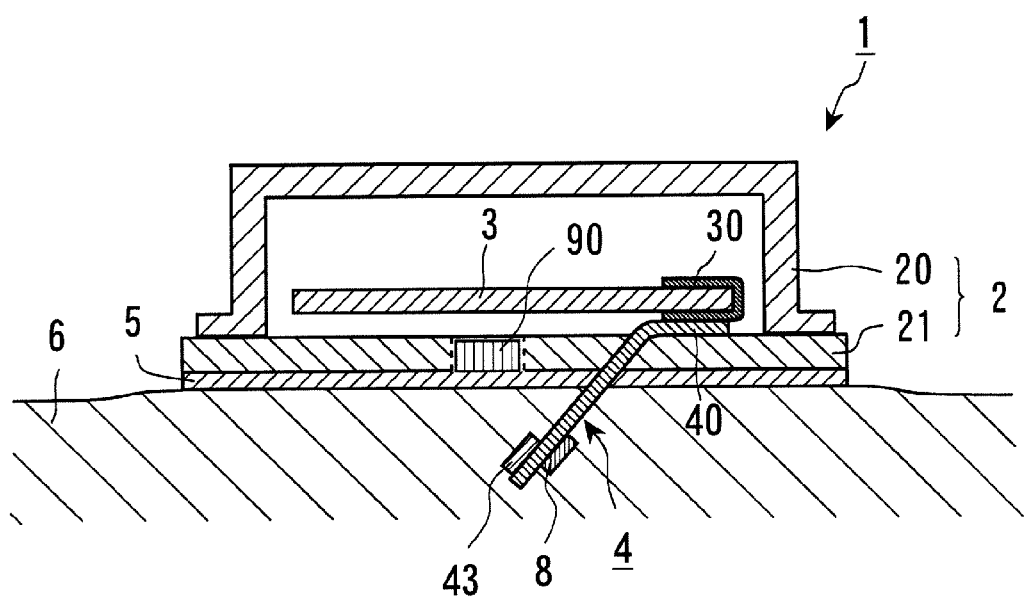
FIG. 16 is a diagram showing an outline of a configuration of the monitoring device according to a fifth working example.

The working examples discussed so far adopt the Peltier device 9 as the temperature adjusting element according to the present invention on the exemplifying and not-limiting basis, however, any inconvenience may not be caused by adopting other configurations without being limited to the Peltier device 9. As illustrated in FIG. 16, a second temperature adjusting element 90 may be disposed as a substitute for the Peltier device 9 depicted in FIG. 1 etc. The second temperature adjusting element 90 includes a micro heater serving as a heat radiation unit, a heat sink serving as a heat absorbing unit, a thermal interface material and a heat spreader or a combination thereof.

Figure 17:
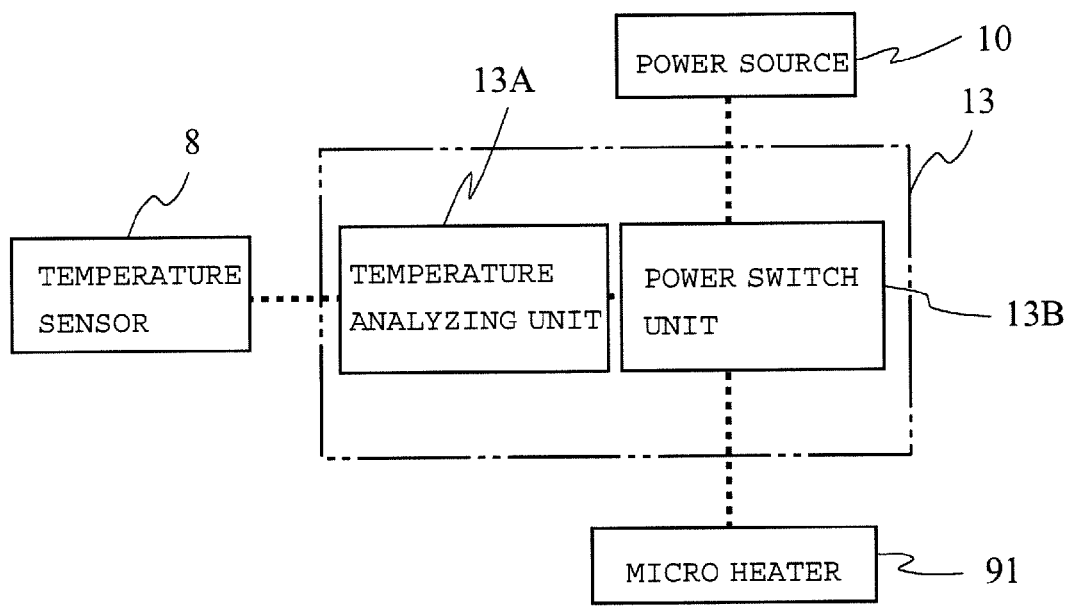
FIG. 17 is a block diagram showing an outline of a configuration of the temperature control unit according to the fifth working example.

FIG. 17 is a block diagram illustrating an outline of a configuration of the temperature control unit in the fifth working example. The temperature control unit 13 in the illustrated configuration includes the temperature analyzing unit 13A and the power switch unit 13B but does not include the current switching unit 13C depicted in FIG. 6. A micro heater 91 of the second temperature adjusting element 90 is connected to the power switch unit 13B and adjusts a quantity of the heat radiated from the micro heater 91 by controlling the voltage applied to the micro heater 91 from the power switch unit 13B. As described above, the second temperature adjusting element 90 has the heat sink serving as the heat absorbing unit, the thermal interface material and the heat spreader (unillustrated), and, in a state of applying none of the drive voltage to the micro heater 91 from the power switch unit 13B, the heat is passively absorbed by these heat absorbing units, thereby enabling a decrease in detected ambient temperature THs to be accelerated.

Accordingly, the micro heater 91 is operated by applying the drive voltage to the micro heater 91 from the power switch unit 13B on the occasion of increasing the detected ambient temperature THs, and the operation thereof is halted by stopping the application of the voltage to the micro heater 91, whereby the detected ambient temperature THs can be adjusted in an unrestricted manner. For example, in the processing flow of FIG. 7, in step S107, the micro heater 91 is operated by switching ON the power switch unit 13B, thereby increasing the detected ambient temperature THs. While on the other hand, in step S108, the operation of the micro heater 91 is halted by switching OFF the power switch unit 13B, thereby decreasing the detected ambient temperature THs. Note that it is possible to omit the step of switching OFF the power switch unit in step S103.

Herein, the micro heater 91 itself is well known, and hence the detailed explanation thereof is herein omitted, however, available heat emitting elements are, e.g., a laminated exothermic member described in Japanese Patent Laid-Open Publication No. S53-122942, an exothermic member for a minute chemical device described in Japanese Patent Laid-Open Publication No. 2002-090357, surface exothermic members described in Japanese Patent Laid-Open Publication No. 2002-025757 and Japanese Patent Laid-Open Publication No. H07-014664, etc. Similarly, the heat sink may involve using heat sinks employed for an in vivo embedding type cooling device illustrated in FIG. 2 of Japanese Patent Laid-Open Publication No. 2007-209523 and in FIGS. 1-4 of Japanese Patent Laid-Open Publication No. 2010-162189, a heat sink used for freeze therapy apparatus for the skin surface that is described in U.S. Pat. No. 4,324,673, and so on. Moreover, the thermal interface material is exemplified by white paste (thermal grease). Materials of the white paste can be exemplified by silicon oil containing aluminum oxide, zinc oxide or boron nitride. Further, the heat spreader can be easily composed of a metal material exhibiting a high thermal conductivity (such as a tungsten/molybdenum/copper-tungsten alloy, a copper-tungsten alloy, aluminum nitride ceramics, etc). Note that the second temperature adjusting element 90 according to the fifth working example can be applied to the layout examples depicted in FIGS. 8-15.

Sixth Working Example

Figure 18:
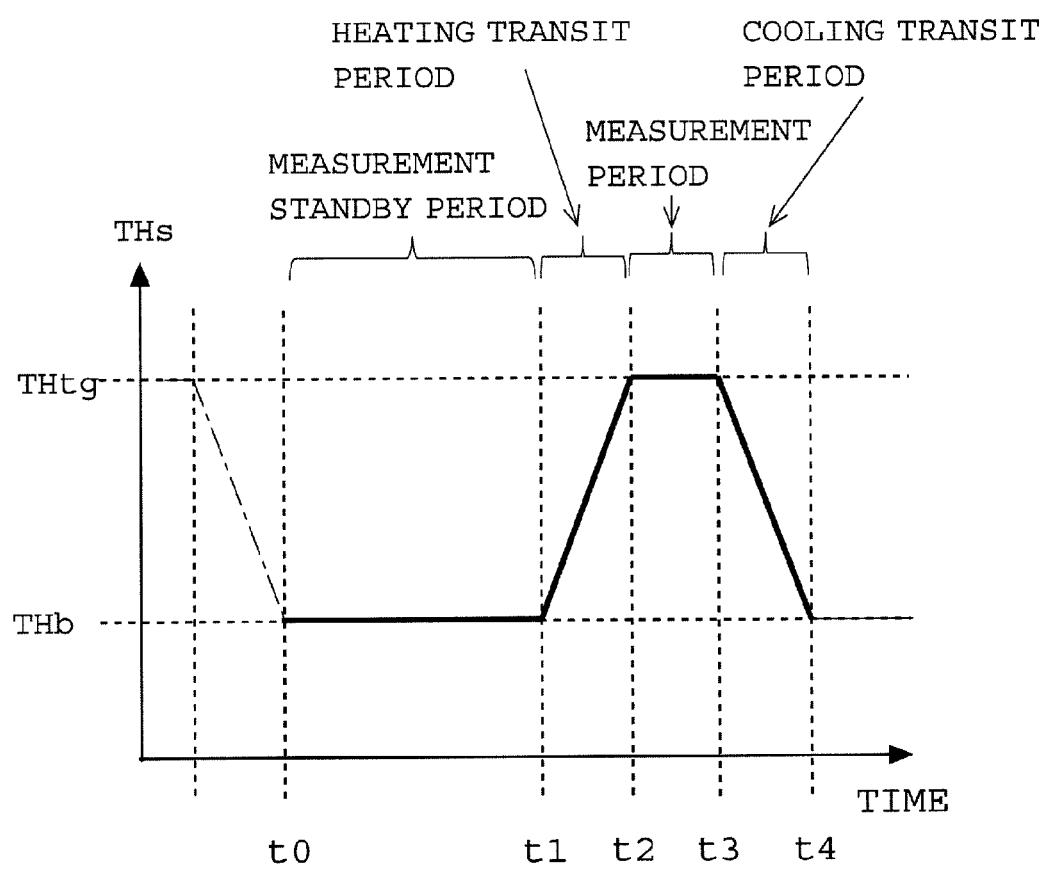
FIG. 18 is a timing chart showing a measurement cycle of the glucose concentration in a sixth working example.

Next, variations different from those in the first working example with respect to contents of the control according to the monitoring device 1 will be explained. An outline of a configuration of the monitoring device 1 according to a sixth working example is the same as those depicted in FIGS. 1-6. FIG. 18 is a timing chart illustrating a measurement cycle of the glucose concentration according to the glucose sensor 4 of the monitoring device 1 in the sixth working example. In the example of FIG. 18, t0-t4 defines one measurement cycle. A period of t2-t3 is a "measurement period" of which the subject substance is measured by use of the glucose sensor 4, and a period of t0-t1 is a "measurement standby period" for which the subject substance is not measured by employing the glucose sensor 4.

Herein, an optimum temperature of the oxidoreductase in the immobilized enzyme unit 43 of the glucose sensor 4 is, e.g., approximately 36° C.-37° C., and the sensor sensitivity is extremely high in this temperature range. If the temperature of the immobilized enzyme unit 43 shifts to a high temperature from the optimum temperature zone, inactivation of the enzyme occurs, which might become a factor for shortening a life-span of the sensor due to the deterioration etc. On the other hand, in the case of measuring the glucose concentration at a lower temperature than the optimum temperature zone in order to prevent the inactivation of the enzyme in the immobilized enzyme unit 43, the reliability on the output result of the glucose sensor 4 might be decreased.

Such being the case, under the temperature adjustment control according to the sixth working example, in order to establish both of restraint of the deterioration in the glucose sensor 4 and improvement of the reliability and the reproducibility related to the measured result of the glucose concentration, the detected ambient temperature THs is adjusted to the target setting temperature THtg during the measurement period and is adjusted to a standby target setting temperature THb during the measurement standby period. The standby target setting temperature THb is a target temperature given on the occasion of adjusting the detected ambient temperature THs during the measurement standby period and is set to a temperature lower than the target setting temperature THtg.

At the measurement cycle, when shifting to the measurement period (t2-t3) from the measurement standby period (t0-t1), the Peltier device 9 performs the heating control, thereby raising the detected ambient temperature THs up to the target setting temperature THtg. During the measurement period (t2-t3), the glucose sensor 4 detects the subject substance once or a plurality of times, thus measuring the glucose concentration. Thereafter, when shifting to the measurement standby period from the measurement period, the Peltier device 9 carries out the cooling control, thereby decreasing the detected ambient temperature THs down to the standby target setting temperature THb. Note that a transit period (t1-t2) to the measurement period from the measurement standby period is referred to as a "heating transit period", and a transit period (t3-t4) to the measurement standby period from the measurement period is termed a "cooling transit period".

The measurement cycle illustrated in FIG. 18 is an exemplification and can be modified properly. Further, a length of one measurement cycle (t0-t4) and a ratio of the measurement time and the measurement standby time may be changed corresponding to an area of the Peltier device 9 (the temperature adjusting element). Note that if the Peltier device 9 has a small area, the heating transit period and the cooling transit period can be reduced as compared with the case of having a larger area. Namely, it is feasible to decrease the ratio occupied by the heating transit period and the cooling transit period at the measurement cycle. As a result, a degree of freedom can be increased on the occasion of setting the ratio of the measurement period and the measurement standby period.

Figure 19:
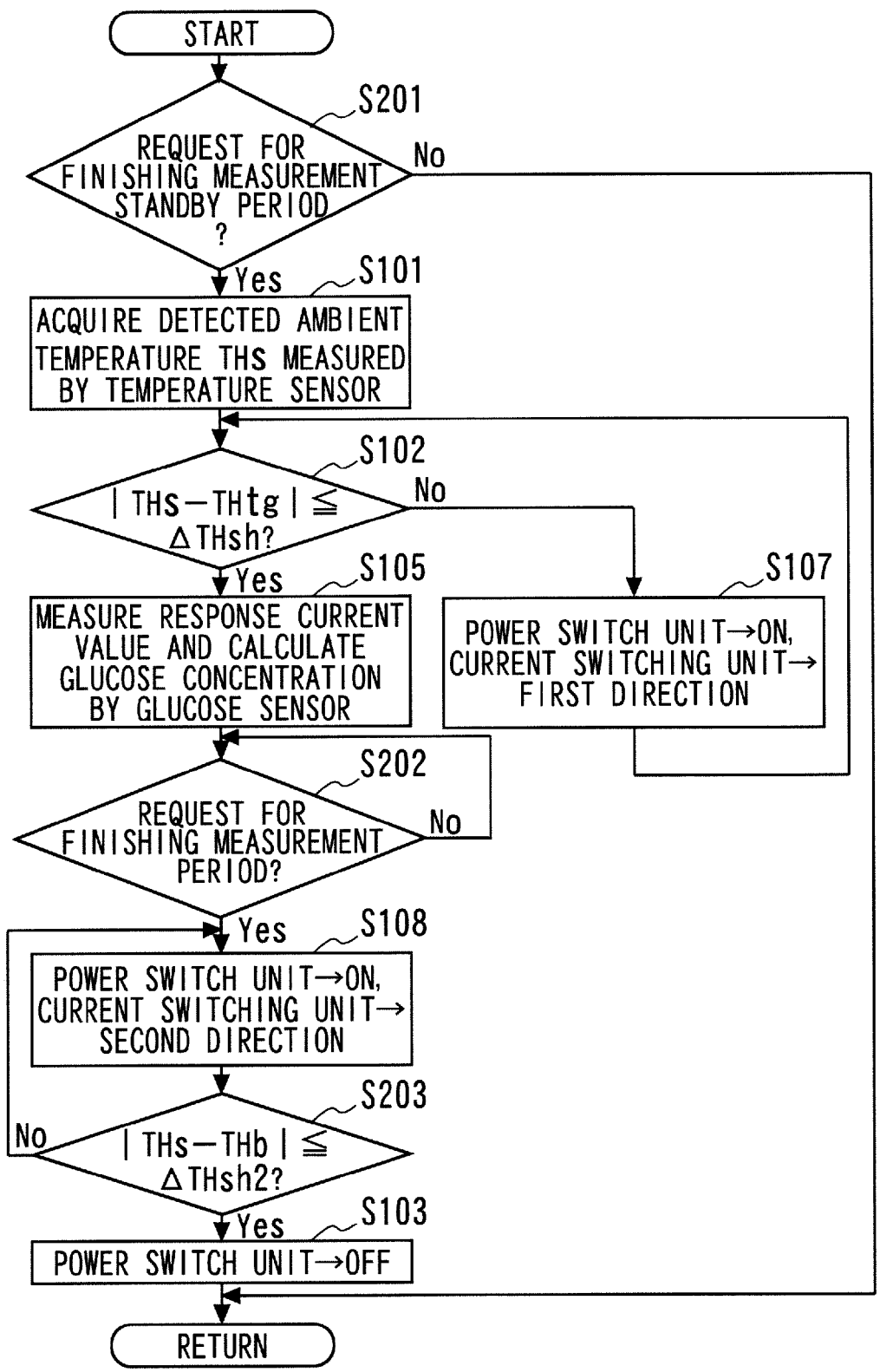
FIG. 19 is a flowchart showing a second control routine when the monitoring device measures the glucose concentration in the sixth working example.

FIG. 19 is a flowchart illustrating a second control routine when the monitoring device 1 in the sixth working example measures the glucose concentration. Steps of executing the same processes of the control routine illustrated in FIG. 7 are marked with the same reference numerals and symbols, and the detailed descriptions thereof are omitted. The control program related to the second control routine is also stored in the ROM etc of the control computer 3 and is executed by the processor at the interval of the predetermined period of time.

In step S201, the temperature control unit 13 determines whether there is a request for finishing the measurement standby period at the present or not. The control computer 3 is equipped with a timer (timer device) for measuring the time, and the storage unit 14 is stored with the data about the measurement cycle as shown in FIG. 18. The temperature control unit 13 refers to the time measured by the timer and the data about the measurement cycle that is stored in the storage unit 14, and determines that the measurement standby period finishing request is given at a point of time when reaching the timing corresponding to t1 in FIG. 18. Note that the timing (t1 in FIG. 18) of issuing the measurement standby period finishing request may be set as timing of advancing by a predetermined period of time from the start timing (t2 in FIG. 18) of the measurement period.

When determining in this step that there is the measurement standby period finishing request, the operation proceeds to step S101, and, whereas if not, the present routine is temporarily terminated. In step S101, the temperature control unit 13 acquires the detected ambient temperature THs based on the output signal of the temperature sensor 8. Subsequently, in step S102, the temperature control unit 13 compares the detected ambient temperature THs with the target setting temperature THtg. The temperature control unit 13, in the case of determining that the absolute value of the difference between the detected ambient temperature THs and the target setting temperature THtg falls within the range of the specified temperature difference ΔTHsh (|THs−THtg|≤ΔTHsh), decides that the detected ambient temperature THs is substantially coincident with the target setting temperature THtg, and the operation proceeds to step S105.

While on the other hand, if it is determined in step S102 that the absolute value of the difference between the detected ambient temperature THs and the target setting temperature THtg does not fall within the range of the specified temperature difference ΔTHsh (|THs−THtg|>ΔTHsh), the operation proceeds to step S107. In step S107, the temperature control unit 13 performs the control to switch ON the power switch unit 13B, and controls the current switching unit 13C so that the Peltier device 9 is supplied with the current in the first direction. With this control operation, the skin in the vicinity of the Peltier device 9 is heated. Upon finishing the process in step S107, the operation loops back to step S102. In the process of step S102, if determined to be negative again (S102: No), the operation proceeds to step S107 described above, however, in this case the operation is in the state of having already supplied the electric current in the [first direction] to the Peltier device 9, and therefore, after the as-is state has been kept for a fixed period of time in step S107, the operation again loops back to step S102. As a result, this heating process continues till the detected ambient temperature THs comes to the target setting temperature THtg.

In step S105, the glucose concentration is measured. To be specific, the sensor control unit 12 applies the voltage to between the electrodes 42 of the glucose sensor 4 and calculates the glucose concentration (the blood glucose level) on the basis of the acquired response current value. The glucose concentration in this step may be measured once and may also be measured plural times.

Upon finishing the process in step S105, the operation proceeds to step S202. In step S202, the temperature control unit 13 determines whether there is a request for finishing the measurement period at the present or not. The temperature control unit 13 refers to, e.g., the time measured by the timer and the data about the measurement cycle that is stored in the storage unit 14, and determines that the measurement period finishing request is given at a point of time when reaching the timing corresponding to t3 in FIG. 18. If determined to be negative in this step, after standing by for the fixed period of time, the determination related to this step is again made repeatedly, and, if determined to be affirmative, the operation proceeds to step S108. Note that the timing (t3 in FIG. 18) when the measurement period finishing request is issued may also be set as timing delayed by a predetermined period of time from the start timing (t2 in FIG. 18) of the measurement period.

In step S108, the temperature control unit 13 performs the control to switch ON the power switch unit 13B, and controls the current switching unit 13C so that the Peltier device 9 is supplied with the current in the second direction. With this control operation, the heat of the skin in the vicinity of the Peltier device 9 is absorbed, thus cooling the skin surface. Then, the cool down temperature of the skin surface is transferred to the glucose sensor 4, thereby cooling the immobilized enzyme unit 43. Upon finishing the process in step S108, the operation proceeds to step S203.

In step S203, the temperature control unit 13 acquires the detected ambient temperature THs on the basis of the output signal of the temperature sensor 8. Subsequently, in step S203, the temperature control unit 13 compares the detected ambient temperature THs with the standby target setting temperature THb, and determines whether or not an absolute value of a difference therebetween falls within a range of a second specified temperature difference ΔTHsh2. As described above, the standby target setting temperature THb is the target temperature given when adjusting the detected ambient temperature THs during the measurement standby period and is set to the temperature lower than the target setting temperature THtg.

If determined to be affirmative in step S203 (|THs−THg|≤ΔTHsh2), the detected ambient temperature THs gets coincident with the standby target setting temperature THb or a temperature that is sufficiently approximate to the standby target setting temperature THb. Whereas if determined to be negative in step S203 (|THs−THg|>ΔTHsh2), the operation loops back to the process in step S108. When the operation thus loops back to the process in step S108, the operation is in the state of having already supplied the electric current in the second direction to the Peltier device 9, and therefore, after the as-is state has been kept for a fixed period of time in step S108, the operation again proceeds to step S203. As a result, this cooling process of the Peltier device 9 continues till the detected ambient temperature THs descends down to the standby target setting temperature THb. If determined to be affirmative in step S203, the detected ambient temperature THs is determined to decrease down to the standby target setting temperature THb. Subsequently, the operation proceeds to step S103, and, after the power switch unit 13B has been switched OFF, the present routine is temporarily finished.

As described above, under the temperature adjustment control according to the sixth working example, the detected ambient temperature THs is adjusted to be coincident with the target setting temperature THtg during the measurement period of each measurement cycle and is maintained to the standby target setting temperature THb set on the lower temperature side than the target setting temperature THtg during the measurement standby period. Therefore, the temperature ambient to the immobilized enzyme unit 43 of the glucose sensor 4 is kept in the optimum temperature zone of the enzyme activity only during the measurement period of each measurement cycle and can be maintained in the temperature zone on the lower temperature side than the optimum temperature zone during other periods. Accordingly, it is possible to establish both of the restraint of the deterioration in the glucose sensor 4 and the improvement of the reliability and the reproducibility of the measured result.

Note that the detected ambient temperature THs is decreased positively down to the standby target setting temperature THb during the measurement standby period in the control example given above, however, for instance, the setting during the measurement standby period may be ended up with simply keeping the Peltier device 9 in a non-operating state. In this case, the Peltier device 9 does not perform the cooling control, which therefore leads to saving the drive power of the Peltier device 9. Further, the detected ambient temperature THs decreases during the measurement standby period as the factors may be, and it therefore follows that the temperature of the immobilized enzyme unit 43 does not shift on the higher temperature side than the optimum temperature zone.

Seventh Working Example

In a seventh working example, the monitoring device 1 implements setting value adjustment control for adjusting the target setting temperature THtg under the temperature adjustment control. This setting value adjustment control is conducted based on the measured result of the glucose concentration acquired by the monitoring device 1 and a second monitoring device 50 that will be described later on. A hardware configuration of the monitoring device 1 according to the seventh working example is the same as in the first working example (see FIGS. 1-6), and the detailed explanation thereof is omitted.

Figure 20:
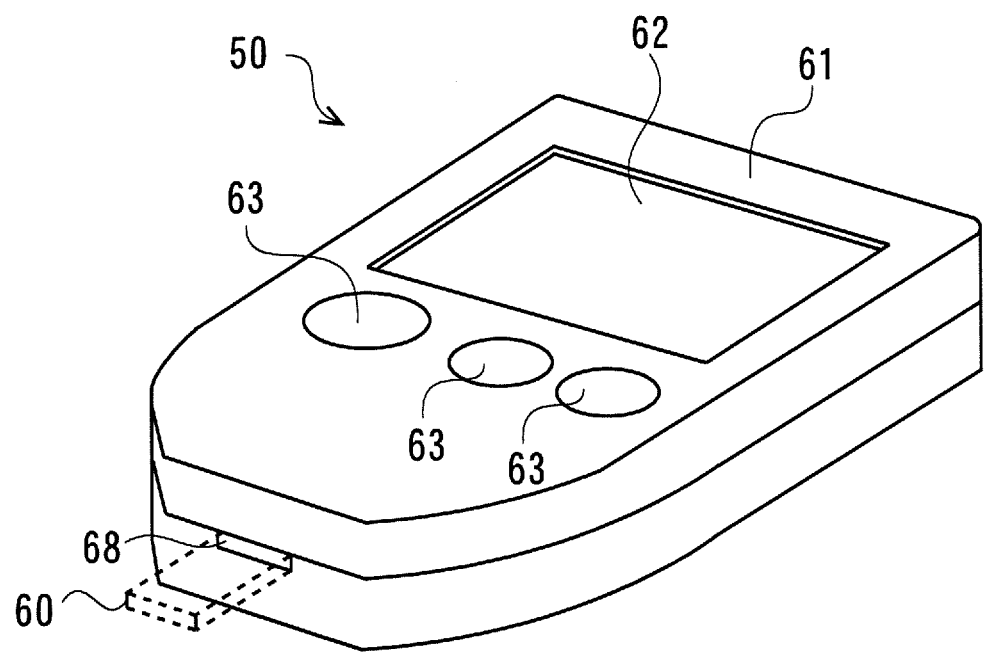
FIG. 20 is a diagram of an outline of a configuration of a second monitoring device.

FIG. 20 is a diagram of an outline of a configuration of the second monitoring device 50. The second monitoring device 50 is an SMBG (Self Monitoring of Blood Glucose) device capable of measuring the glucose concentration (blood glucose level) in the body fluid (blood, interstitial liquid, etc.) captured in vitro, and measures the blood glucose level by use of the blood bled in vitro such as a drop of finger blood. The blood sampled in vitro from the examinee is referred to as a second sample as the case may be.

The second monitoring device 50 measures the glucose concentration of the second sample by an electrochemical technique using a biosensor 60. The second monitoring device 50 includes a housing 61, a display panel 62, an operation button 63 and a sensor insertion port 68. Further, the second monitoring device 50 has, though its illustration is omitted, a circuit board mounted with electronic components such as a CPU, a RAM and a ROM required for predetermined operations (such as applying the voltage and performing the communications with the outside) of the second monitoring device 50.

As shown in FIG. 20, the housing 61 is provided with the display panel 62 and the plurality of operation buttons 63. The plurality of operation buttons 63 is used for executing operations such as setting a variety of measurement conditions and starting/finishing the measurement. The plurality of operation buttons 63 may also be provided on a contact type touch panel. The display panel 62 displays the measured result and an error, and also displays operation procedures and operation states when setting. The display panel 62 is exemplified by a liquid crystal display device, a plasma display panel, a Cathode Ray Tube (CRT) or an electroluminescence panel. The biosensor 60 is a known sensor in which a sample layer containing, e.g., an electron transfer substance and the oxidoreductase is formed on the base plate.

Figure 21:
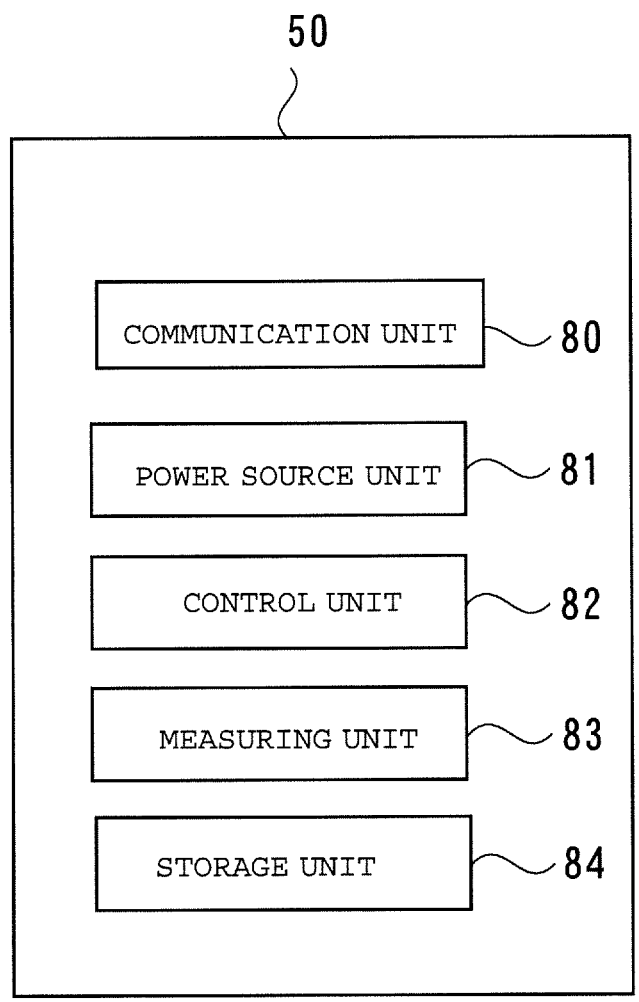
FIG. 21 is a diagram of a functional configuration of the second monitoring device.

Respective functions provided in the second monitoring device 50 will be explained. FIG. 21 is a function block diagram of the second monitoring device 50. The second monitoring device 50 includes a communication unit 80, a power source unit 81, a control unit 82, a measuring unit 83 and a storage unit 84. The communication unit 80 performs the data communications between the monitoring device 1 and the second monitoring device 50. The data communications can involve utilizing, e.g., the wireless communication means. Further, the wired data communications may also be conducted by establishing a connection between the monitoring device 1 and the second monitoring device 50 via a cable of a USB (Universal Serial Bus) etc. The power source unit 81 supplies the electric power for driving the second monitoring device 50. For example, the function as the power source unit 81 may be actualized by use of a button battery having a power voltage on the order or 1V-3V. The control unit 82 controls the communications with, e.g., the monitoring device 1.

The measuring unit 83 measures the glucose concentration (blood glucose level) of the glucose contained in the blood (the second sample) brought into contact with the sensor unit (sample layer) of the biosensor 60. Then, the storage unit 84 gets stored with the glucose concentration measured by the measuring unit 83 in the way of being associated with the measurement time information thereof. The measured result of the glucose concentration in the blood, which is measured by the thus-configured second monitoring device 50, is transmitted to the communication unit 11 in the monitoring device 1 from the communication unit 80 of the second monitoring device 50.

The continuous measurement of the glucose concentration by use of the monitoring device 1 continues over a comparatively long period of time (e.g., approximately one week) in many cases, and hence the sensitivity of the glucose sensor 4 is lowered as the case may be due to the deterioration as the glucose oxidoreductase in the immobilized enzyme unit 43 is affected by repeatedly applying the voltage or due to gradual adhesion/deposition of the cell tissues to and on the periphery of the immobilized enzyme unit 43. Further, if the sensitivity of the glucose sensor 4 declines stepwise as the continuous measurement period elongates, an error might occur between the measurement value of the glucose concentration and a true glucose concentration.

Figure 22:
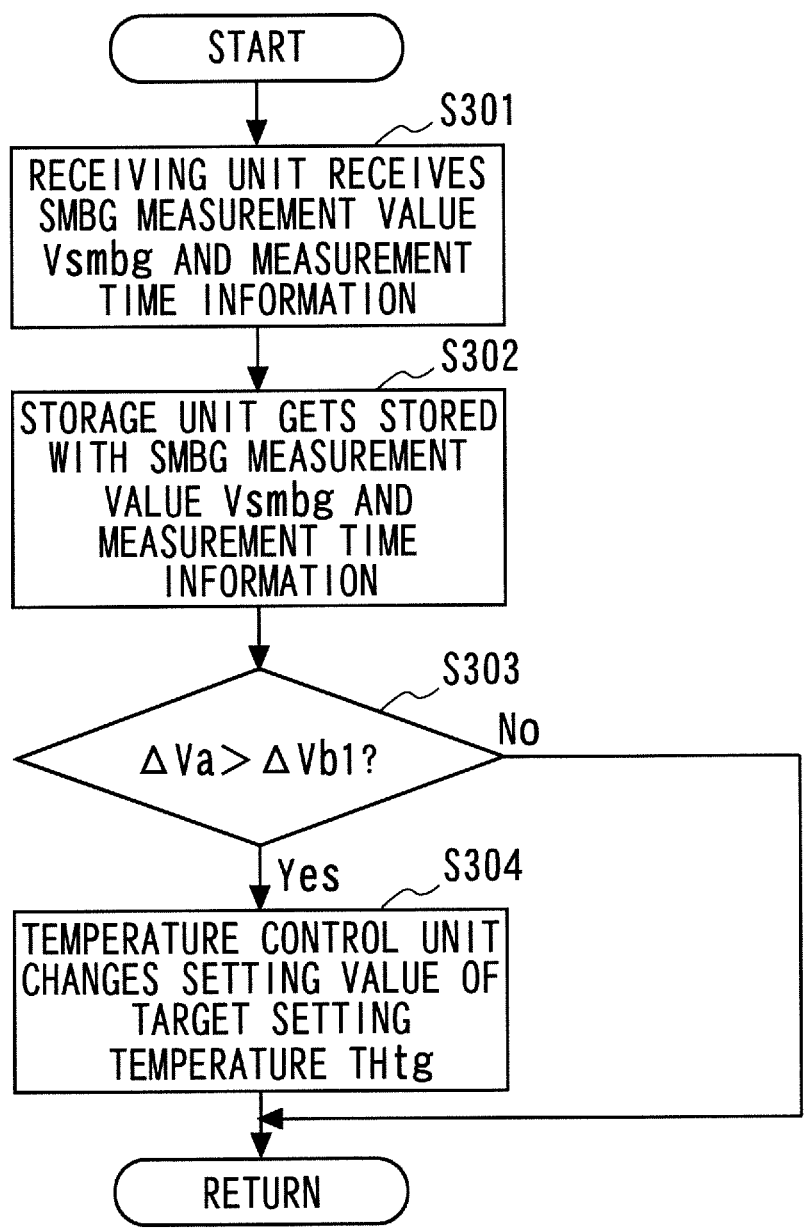
FIG. 22 is a flowchart showing a setting value adjustment control routine according to a seventh working example.

The seventh working example involves periodically performing the following setting value adjustment control when the monitoring device 1 continuously measures the glucose concentration. FIG. 22 is a flowchart showing a setting value adjustment control routine according to the seventh working example. A program related to this control routine is stored in the ROM of the control computer 3 in the monitoring device 1 and is executed as triggered by receiving a setting value adjustment control start signal from the second monitoring device 50.

Upon executing this control routine, in step S301, the communication unit 11 receives, from the communication unit 80 of the second monitoring device 50, the measurement time information and the measurement value (which will hereinafter be termed an "SMBG measurement value Vsmbg" (corresponding to second numerical value information)) when the second monitoring device 50 measures the glucose concentration of the second sample. Then, in step S302, the storage unit 14 in the monitoring device 1 is stored with the SMBG measurement value Vsmbg received by the communication unit 11 in the way of being associated with the measurement time information thereof.

Moreover, the storage unit 14 is stored with the glucose concentration measurement values (which will hereinafter be termed "CGM measurement values Vcgm" (corresponding to first numerical value information)) measured by the sensor control unit 12 up to the present time after starting the continuous measurement of the glucose concentration and with the measurement time information in the way of being associated with each other. When the update data of the SMBG measurement value Vsmbg is added to the storage unit 14, the temperature control unit 13 extracts, in step S303, the measurement time information associated with the updated SMBG measurement value Vsmbg and the CGM measurement value Vcgm measured at the nearest point of time. As a result, the temperature control unit 13 can acquire the CGM measurement value Vcgm and the SMBG measurement value Vsmbg which are measured substantially at the same point of time. Subsequently, the temperature control unit 13 calculates an absolute value between the SMBG measurement value Vsmbg and the CGM measurement value Vcgm (which will hereinafter be referred to as a "measurement absolute error $\Delta Va$").

The temperature control unit 13 determines whether the measurement absolute error $\Delta Va$ exceeds a first reference value $\Delta Vb1$ or not. If the measurement absolute error $\Delta Va$ is determined equal to or smaller than the first reference value $\Delta Vb1$ ($\Delta Va \leq \Delta Vb1$), it is concluded that the glucose sensor 4 has the adequate sensitivity and the glucose concentration contains almost no measurement error. Such being the case, when determining in this step that the measurement absolute error $\Delta Va$ is equal to or smaller than the first reference value $\Delta Vb1$ ($\Delta Va \leq \Delta Vb1$), the present routine is temporarily finished. In this case, this is because the determination is that the sensitivity of the glucose sensor 4 does not need adjusting specially. Whereas if it is determined that the measurement absolute error $\Delta Va$ exceeds the first reference value $\Delta Vb1$ ($\Delta Va > \Delta Vb1$), the operation proceeds to step S304.

In step S304, the temperature control unit 13 changes the setting value of the target setting temperature THtg. Herein, a change width of the target setting temperature THtg is adjusted corresponding to a magnitude of the measurement absolute error $\Delta Va$. A difference of the measurement value, which is acquired by subtracting the CGM measurement value Vcgm from the SMBG measurement value Vsmbg, is expressed by a "measurement error $\Delta Vr$". In this routine, the temperature setting change value $\Delta THtg$ obtained by multiplying the measurement error $\Delta Vr$ by a constant C1 (where C1>0) is added to the present target setting temperature THtg, thus calculating a post-modifying target setting temperature (which will hereinafter be referred to as a "target modified temperature THtgm") (THtgm=THtg+$\Delta THtg$, $\Delta THtg$=C1×$\Delta Vr$). Note that the calculation formula is an exemplification, and the calculation is not limited to this formula. When terminating the process in this step, the present routine is temporarily finished.

The SMBG measurement value Vsmbg is obtained by measuring the glucose concentration in a way that uses, as the sample, the blood sampled in vitro from the examinee. Therefore, the reliability of the measured result thereof is higher than the CGM measurement value Vcgm measured by employing the subcutaneous indwelling type glucose sensor 4. Hence, herein the SMBG measurement value Vsmbg is deemed to be the true glucose concentration.

If the glucose sensor 4 has a low sensitivity, the CGM measurement value Vcgm is lower than the SMBG measurement value Vsmbg in many cases. In this instance, the measurement error $\Delta Vr$ takes the positive value, whereby the temperature setting change value $\Delta THtg$ takes the positive value. As a result, the target setting temperature THtg is corrected on the high-temperature side to thereby accelerate the enzyme activity in the immobilized enzyme unit 43, and it is possible to increase the sensor sensitivity of the glucose sensor 4. While on the other hand, if the sensitivity of the glucose sensor 4 excessively rises, an assumption is that the CGM measurement value Vcgm is higher than the SMBG measurement value Vsmbg. In this case, the measurement error $\Delta Vr$ takes the negative value, whereby the temperature setting change value $\Delta THtg$ also takes the negative value. As a result, the target setting temperature THtg is corrected on the low-temperature side to thereby decelerate the enzyme activity in the immobilized enzyme unit 43, and it is possible to decrease the sensor sensitivity of the glucose sensor 4. As discussed above, the target setting temperature THtg is adjusted corresponding to the magnitude of the measurement error $\Delta Vr$ under this control, thereby enabling the monitoring device 1 to enhance the measurement accuracy of the glucose concentration. Moreover, if the CGM measurement value Vcgm is higher than the SMBG measurement value Vsmbg, the target setting temperature THtg is modified on the low-temperature side, and it is therefore feasible to further surely avoid the occurrence of the deterioration due to such a point that the temperature of the immobilized enzyme unit 43 in the glucose sensor 4 gets higher than the optimum temperature zone of the enzyme.

Under the setting value adjustment control according to the seventh working example, the setting value of the target setting temperature THtg is changed corresponding to the magnitude of the measurement error ΔVr, and hence, even when the deterioration etc is caused as derived from the continuous use of the glucose sensor 4, the sensor sensitivity in the glucose sensor 4 can be properly maintained, with the result that the reliabilities of the measurement accuracy and the measurement result can be enhanced.

Modified Example

Next, a modified example of the setting value adjustment control in the seventh working example will be explained. The storage unit 14 is stored with calibration curve data representing an associative relation between the response current value and the glucose concentration each given from the glucose sensor 4 in the form of a mathematical expression and an associative table. Further, plural sets of calibration curve data are prepared corresponding to the sensor sensitivities of the glucose sensor 4 and are stored in the storage unit 14. In this case, if the measurement absolute error ΔVa exceeds the first reference value ΔVb1, the sensor control unit 12 selects another set of calibration curve data corresponding to the measurement error ΔVr, whereby the glucose sensor 4 may improve the measurement accuracy of the glucose concentration. In such a case also, the calibration curve data count is finite. Therefore, as under the setting value adjustment control described above, the adjustment of the target setting temperature THtg under the temperature adjustment control with reference to the SMBG measurement value Vsmbg transmitted from the side of the second monitoring device 50 is highly effective in minutely adjusting the sensor sensitivity. It is because the setting value adjustment control described above enables the respective sets of calibration curve data to be effectively interpolated.

Figure 23:
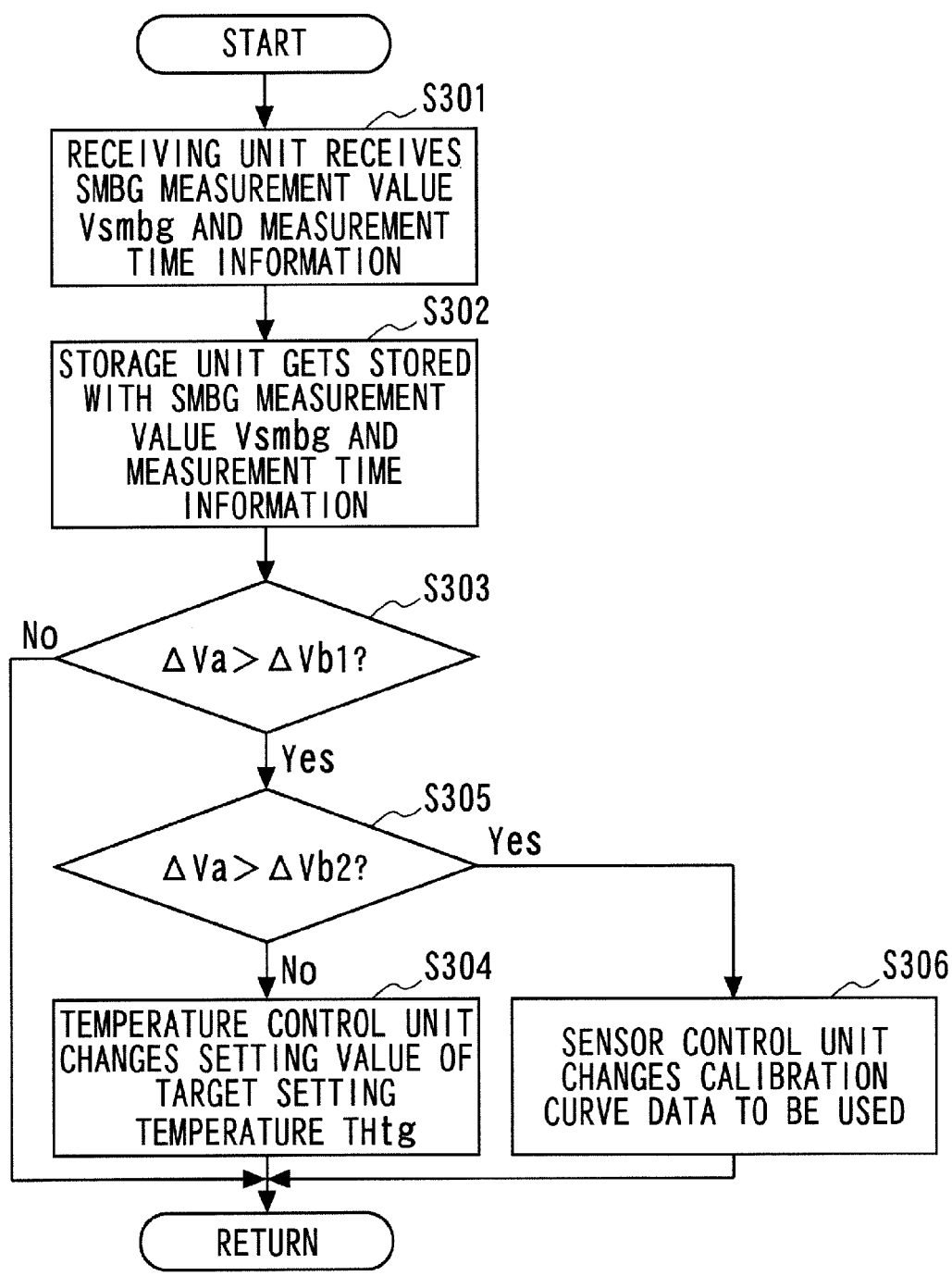
FIG. 23 is a flowchart showing a second setting value adjustment control routine according to the seventh working example.

Moreover, in the flowchart shown in FIG. 22, only one threshold value for the measurement absolute error ΔVa is provided, however, the plurality of threshold values may also be provided. FIG. 23 is a flowchart showing a second setting value adjustment control routine according to the seventh working example. The program related to this control routine is stored in the ROM of the control computer 3 in the monitoring device 1 and is executed as triggered by receiving the setting value adjustment control start signal from the second monitoring device 50. The steps of executing the same processes as those in the processing flow illustrated in FIG. 22 are marked with the same reference numerals and symbols, and the in-depth descriptions thereof are omitted.

In step S303, when determining that the measurement absolute error ΔVa exceeds the first reference value ΔVb1 (ΔVa>ΔVb1), the operation proceeds to step S305. In step S305, the temperature control unit 13 determines whether the measurement absolute error ΔVa exceeds a second reference value ΔVb2 or not. The second reference value ΔVb2 is a threshold value for determining whether the calibration curve data used for calculating the glucose concentration needs changing or not, and is set to a value larger than the first reference value ΔVb1. When determining that the measurement absolute error ΔVa is equal to or smaller than the second reference value ΔVb2 (ΔVb1<ΔVa≤ΔVb2), it is concluded that the calibration curve data used for calculating the glucose concentration does not need changing. In this case, the operation proceeds to step S304, in which the setting value of the target setting temperature THtg is changed corresponding to the magnitude of the measurement absolute error ΔVa.

While on the other hand, when determining the measurement absolute error ΔVa exceeds the second reference value ΔVb2 (ΔVa>ΔVb2), the operation proceeds to step S306. In step S306, the sensor control unit 12 changes the calibration curve data used for calculating the glucose concentration. The sensor control unit 12 reselects the calibration curve data to enhance the sensor sensitivity if the measurement error ΔVr takes the positive value and reselects the calibration curve data to lower the sensor sensitivity if the measurement error ΔVr takes the negative value. Then, upon finishing the process in this step, the present routine is temporarily terminated. Incidentally, in step S306, along with the change in setting (selection) of the calibration curve data, the setting value of the target setting temperature THtg may be changed in the same way as in step S304. With this operation, the sensor sensitivity of the glucose sensor 4 can be corrected more minutely.

According to the control example shown in FIG. 23, when the measurement absolute error ΔVa is comparatively small, the sensitivity of the glucose sensor 4 can be adjusted without reselecting the calibration curve data. Further, even if the deterioration of the glucose sensor 4 progresses due to the elongation of the continuous measurement period of the blood glucose level, it is feasible to expand the adjustment width of the sensor sensitivity of the glucose sensor 4 by reselecting the calibration curve data used for measuring the glucose concentration. Moreover, the target setting temperature THtg is corrected together as the necessity may arise, whereby it is possible to establish both of ensuring the adjustment width of the sensor sensitivity of the glucose sensor 4 and making the more minute adjustment. In the seventh working example, the first reference value ΔVb1 corresponds to a first threshold value according to the present invention.

Eighth Working Example

Figure 24:
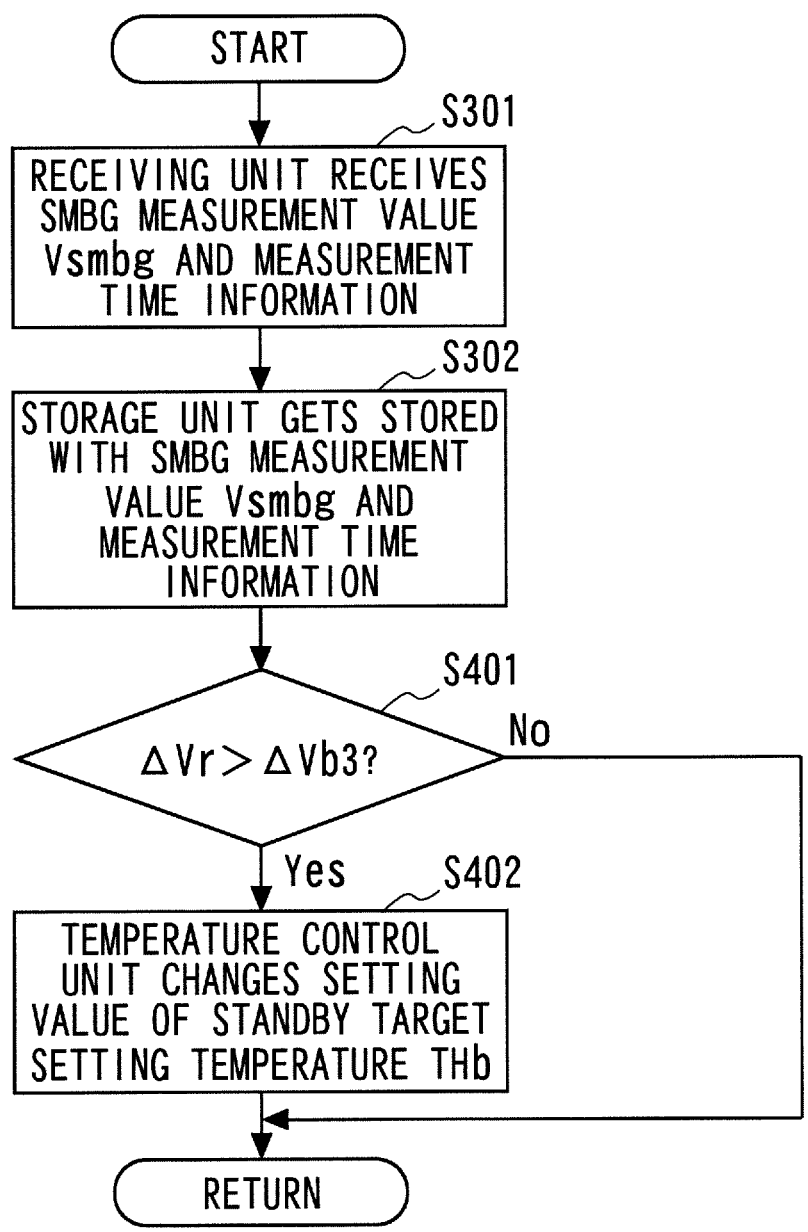
FIG. 24 is a flowchart showing a setting value adjustment control routine according to an eighth working example.

The seventh working example has discussed the control example for modifying the setting value of the target setting temperature THtg during the measurement period of each measurement cycle, however, an eighth working example will discuss a control example for adjusting a setting value of the standby target setting temperature THb during the measurement standby period. Hardware configurations of the monitoring device 1 and the second monitoring device 50 according to the eighth working example are the same as the hardware configurations in the sixth working example. FIG. 24 is a flowchart showing a setting value adjustment control routine according to the eighth working example. The program related to this control routine is stored in the ROM of the control computer 3 in the monitoring device 1 and is executed as triggered by receiving the setting value adjustment control start signal from the second monitoring device 50. The steps of executing the same processes as those in the processing flow illustrated in FIGS. 22 and 23 are marked with the same reference numerals and symbols, and the in-depth descriptions thereof are omitted.

Upon executing the present control routine, in step S301, the communication unit 11 receives, from the communication unit 80 of the second monitoring device 50, the SMBG measurement value Vsmbg measured from the second sample by the second monitoring device 50 and the measurement time information associated therewith. In step S302, the storage unit 14 is stored with the SMBG measurement value Vsmbg received by the communication unit 11 in the way of being associated with the measurement time information. When update data of the SMBG measurement value Vsmbg is added to the storage unit 14, the temperature control unit 13 extracts, in subsequent step S401, data (information) of the CGM measurement value Vcgm measured at the time nearest to the measurement time associated with the SMBG measurement value Vsmbg. This scheme enables the temperature control unit 13 to acquire the CGM measurement value Vcgm and the SMBG measurement value Vsmbg that are measured substantially at the same point of time (approximately at the same point of time).

The temperature control unit 13 calculates the measurement error $\Delta Vr$ by subtracting the CGM measurement value Vcgm from the acquired SMBG measurement value Vsmbg. Then, the temperature control unit 13 determines whether the measurement error $\Delta Vr$ exceeds a third reference value $\Delta Vb3$ or not. The third reference value $\Delta Vb3$ is a threshold value for determining whether or not the sensor sensitivity declines due to the adhesion/deposition of the subcutaneous tissues and the deterioration of the immobilized enzyme unit 43. Herein, when determining that the measurement error $\Delta Vr$ is equal to or smaller than the third reference value $\Delta Vb3$ ($\Delta Vr \leq \Delta Vb3$), it is concluded that the sensor sensitivity has almost no decline due to the deterioration etc of the immobilized enzyme unit 43 of the glucose sensor 4, and the present routine is temporarily terminated. While on the other hand, when determining that the measurement error $\Delta Vr$ exceeds the third reference value $\Delta Vb3$ (($\Delta Vr > \Delta Vb3$), it is concluded that the sensor sensitivity declines due to the deterioration etc of the immobilized enzyme unit 43, and in this case the operation proceeds to step S402.

In step S402, the temperature control unit 13 changes the setting value of the standby target setting temperature THb during the measurement standby period of each measurement cycle. A change width of the standby target setting temperature THb is adjusted corresponding to the magnitude of the measurement error $\Delta Vr$. In the present routine, the temperature setting change value $\Delta THb$ acquired by multiplying the measurement error $\Delta Vr$ by a constant C2 (where C2>0) is set as a post-modifying standby target setting temperature (which will hereinafter be termed a "standby target modified temperature THbm") through the subtraction from the present standby target setting temperature THb (THbm=THbg+$\Delta THb$, $\Delta THb$=C2×$\Delta Vr$). Herein, if the SMBG measurement value Vsmbg is larger than the CGM measurement value Vcgm, the temperature setting change value $\Delta THb$ takes the positive value, and hence the standby target modified temperature THbm is changed on the lower temperature side than the present standby target setting temperature THb. Upon finishing the process in this step, the present routine is temporarily terminated. Note that the calculation formula is an exemplification, and the calculation is not limited to this formula.

Thus, under the setting value adjustment control according to the eighth working example, the setting value of the standby target setting temperature THb during the measurement standby period is adjusted corresponding to the magnitude of the measurement error $\Delta Vr$, and therefore it is feasible to hinder the deterioration of the glucose sensor 4 and to delay the progress thereof. Accordingly, even when the continuous measurement period of the glucose concentration elongates, the measurement accuracy can be restrained from decreasing. In the eighth working example, the third reference value $\Delta Vb3$ corresponds to a second threshold value according to the present invention.

Modified Example

Figure 25:
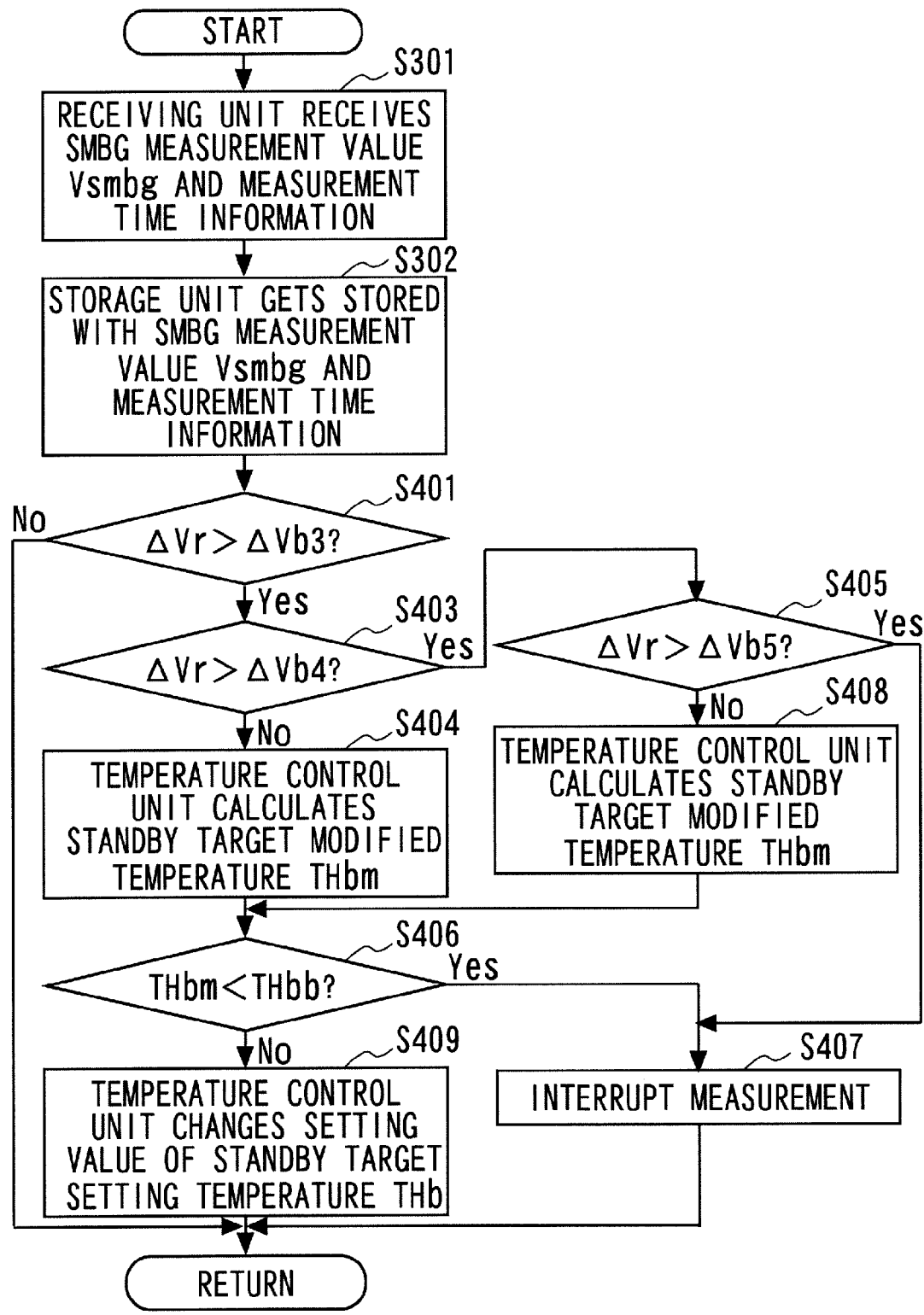
FIG. 25 is a flowchart showing a second setting value adjustment control routine according to the eighth working example.

Next, a modified example of the setting value adjustment control in the eighth working example will be described. FIG. 25 is a flowchart showing a second setting value adjustment control routine according to the eighth working example. The program related to this control routine is stored in the ROM of the control computer 3 in the monitoring device 1 and is executed as triggered by receiving the setting value adjustment control start signal from the second monitoring device 50. In the flowchart shown in FIG. 24, only one threshold value is provided for the measurement error $\Delta Vr$, however, the plurality of threshold values is provided herein. In FIG. 25, the steps of executing the same processes as those in the processing flow illustrated in FIGS. 22 through 24 are marked with the same reference numerals and symbols, and the in-depth descriptions thereof are omitted.

In the present control routine, in step S401, when determining that the measurement error $\Delta Vr$ exceeds the third reference value $\Delta Vb3$ ($\Delta Vr > \Delta Vb3$), the operation proceeds to step S403. In step S403, the temperature control unit 13 determines whether the measurement error $\Delta Vr$ exceeds a fourth reference value $\Delta Vb4$ or not. When determining that the measurement error $\Delta Vr$ is equal to or smaller than the fourth reference value $\Delta Vb4$ ($\Delta Vb3 < \Delta Vr \leq \Delta Vb4$), the operation proceeds to step S404, and, whereas if not ($\Delta Vr > \Delta Vb4$), the operation proceeds to step S405. Incidentally, when determining in step S401 that the measurement error $\Delta Vr$ is equal to or smaller than the third reference value $\Delta Vb3$ ($\Delta Vr \leq \Delta Vb3$), the present routine is temporarily terminated.

In step S404, the temperature control unit 13 calculates the standby target modified temperature THbm in a way that subtracts, from the present standby target setting temperature THb, the temperature setting change value $\Delta THb$ obtained by multiplying the measurement error $\Delta Vr$ by the constant C2 (where C2>0) (THbm=THb–$\Delta THb$, $\Delta THb$=C2×$\Delta Vr$). Note that the calculation formula is an exemplification, and the calculation is not limited to this formula. Upon finishing the process in step S404, the operation proceeds to step S406. A content of the process in step S406 will be described later on, and hence, at first, a content of the process in step S405 is herein explained.

In step S405, the temperature control unit 13 determines whether the measurement error $\Delta Vr$ exceeds a fifth reference value $\Delta Vb5$ or not. The fifth reference value $\Delta Vb5$ is a threshold value set to a value larger than the fourth reference value $\Delta Vb4$, and, if the measurement error $\Delta Vr$ exceeds the fifth reference value $\Delta Vb5$, it is concluded that the use of the glucose sensor 4 should be interrupted because of an outstanding progress of the deterioration of the immobilized enzyme unit 43. In step S405, when determining that the measurement error $\Delta Vr$ exceeds the fifth reference value $\Delta Vb5$ ($\Delta Vr > \Delta Vb5$), the operation proceeds to step S407. In step S407, the temperature control unit 13 outputs, to the sensor control unit 12, an instruction (instruction signal) having a content of stopping the measurement of the glucose concentration by the glucose sensor 4, thus interrupting the measurement of the glucose concentration (step S407). In this case, the monitoring device 1 informs the user that the continuous measurement of the glucose concentration is interrupted and informs the user of information having a content of prompting the user to replace the glucose sensor 4 with a new glucose sensor 4 by displaying these items of information on the display panel 15 of the portable display machine 16. Alternatively, the monitoring device 1 may give an alarm having a content of prompting the user to replace the glucose sensor 4 with a new glucose sensor 4 in order to call the user's attention without forcibly interrupting the continuous measurement of the glucose concentration. Upon finishing the process in this step, the present routine is temporarily terminated.

Further, in step S405, when determining that the measurement error ΔVr is equal to or smaller than the fifth reference value ΔVb5 (ΔVb4<ΔVr≤ΔVb5), the operation proceeds to step S408. In step S408, the temperature control unit 13 calculates the standby target modified temperature THbm in a way that subtracts, from the present standby target setting temperature THb, a temperature setting change value ΔTHb' obtained by multiplying the measurement error ΔVr by a constant C3 (where C3>C2) (THbm=THb−ΔTHb', ΔTHb'=C3×ΔVr). Note that the calculation formula is an exemplification, and the calculation is not limited to this formula.

The fifth reference value ΔVb5 is a threshold value set to a value larger than the fourth reference value ΔVb4, and hence, if determined to be affirmative in step S403, i.e., when determining that the measurement error ΔVr exceeds the fourth reference value ΔVb4, it is concluded that the deterioration of the glucose sensor 4 shows more of the progress of the deterioration of the glucose sensor 4 than in the case of making the negative determination. By contrast, the constant C3 defined as a reduction coefficient of the standby target setting temperature THb is set larger than the constant C2, so that the temperature setting change value ΔTHb' calculated in step S408 is larger than the temperature setting change value ΔTHb calculated in step S404. As a result, the decrease width of the standby target setting temperature THb can be set larger as the glucose sensor 4 comes to have a higher degree of its deterioration, thereby enabling the progress of the deterioration of the glucose sensor 4 to be preferably retarded.

Upon finishing the process in step S408, the operation proceeds to step S406. The temperature control unit 13 determines whether the standby target modified temperature THbm calculated in step S404 or S408 is lower than a predetermined allowable minimum temperature THbb or not. Herein, the allowable minimum temperature THbb is the minimum temperature of the detected ambient temperature THs, at which the examinee feels neither a sense of discomfort nor displeasure. The allowable minimum temperature THbb can be also preset and can be set variably by accepting a manual input from the user. In step S406, if determined to be affirmative (THbm<THbb), the operation proceeds to step S407. Whereas if determined to be negative (THbm≤THbb), the operation proceeds to step S409.

Note that the determining process in step S406, i.e., the process of determining whether or not the standby target modified temperature THbm is lower than the allowable minimum temperature THbb, is not indispensable but may be omitted. In this case, it is preferable that the operation proceeds directly to step S409. In step S409, the temperature control unit 13 changes the setting value of the standby target setting temperature THb to the standby target modified temperature THbm from the present setting value. This standby target modified temperature THbm is a value calculated in step S404 or S408. Upon finishing the process in this step, the present routine is temporarily terminated.

As discussed above, under the control according to this modified example, the plurality of threshold values is provided for the magnitudes of the measurement errors ΔVr, and it is therefore feasible to properly take, corresponding to the degree of deterioration, the measure for preventing the deterioration of the glucose sensor 4 from progressing. Furthermore, on the occasion of setting the standby target modified temperature THbm, the allowable minimum temperature THbb is set so that the detected ambient temperature THs does not become excessively low, and hence the examinee feels neither the sense of discomfort nor the displeasure.

Moreover, under the setting value adjustment control according to the eighth working example, the case of adjusting the standby target setting temperature THb during the measurement standby period of each measurement cycle has been discussed, however, the control according to the sixth working example described above, i.e., the adjustment of the target setting temperature THtg during the measurement period may be carried out together.

Ninth Working Example

A ninth working example involves, on the occasion of the glucose continuous measurement, adjusting the detected ambient temperature THs during both of the measurement period and the measurement standby period of the measurement cycle on the basis of a difference between the CGM measurement values Vcgm acquired at first timing Tm1 and second timing Tm2 before an elapse of the predetermined first period ΔTm1 (corresponding to a predetermined period) from the first timing Tm1. The hardware configurations of the monitoring device 1 and the second monitoring device 50 according to the ninth working example are the same as those in the seventh working example.

Figure 26:
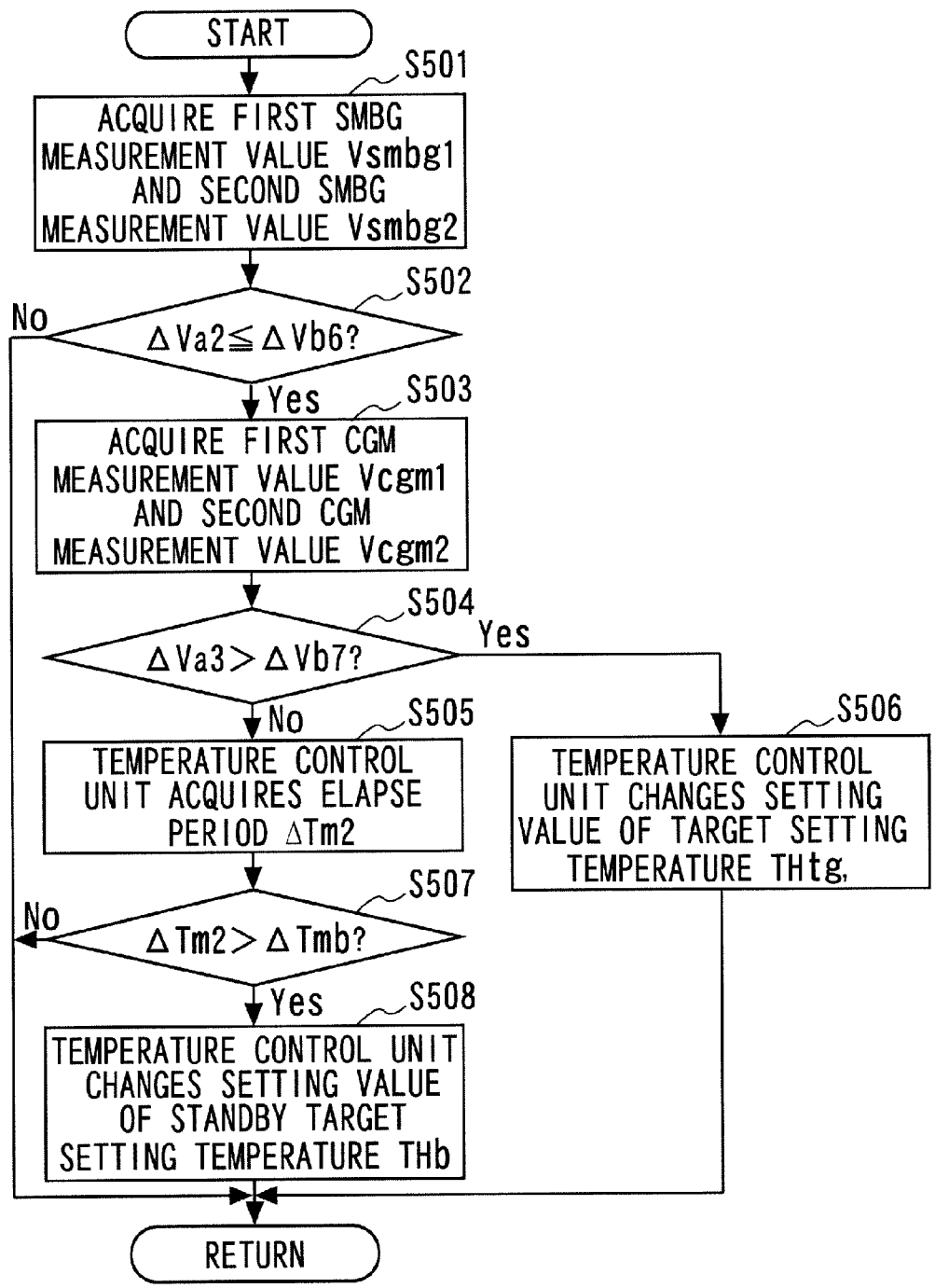
FIG. 26 is a flowchart showing a setting value adjustment control routine according to a ninth working example.

FIG. 26 is a flowchart showing a setting value adjustment control routine according to the ninth working example. The program related to this control routine is stored in the ROM of the control computer 3 in the monitoring device 1. The steps of executing the same processes as those in the processing flow illustrated in FIGS. 22 through 25 are marked with the same reference numerals and symbols, and the in-depth descriptions thereof are omitted.

In step S501, the temperature control unit 13 accesses the storage unit 14 and thus acquires the updated SMBG measurement value Vsmbg via the communication unit 11. Then, the temperature control unit 13 acquires the SMBG measurement value Vsmbg (which will hereinafter be termed a "second SMBG measurement value Vsmbg2") stored in the storage unit 14 at the nearest point of time which traces back to at least the first period ΔTm1 or longer from the point of time when measuring the acquired updated SMBG measurement value Vsmbg (which will hereinafter be termed a "first SMBG measurement value Vsmbg1").

Subsequently, in step S502, the temperature control unit 13 determines whether or not an absolute value of a difference (which will hereinafter be termed a "second measurement absolute error ΔVa2") between the first SMBG measurement value Vsmbg1 and the second SMBG measurement value Vsmbg2 is equal to or smaller than a sixth reference value ΔVb6 (a third threshold value). If the second measurement absolute error ΔVa2 is equal to or smaller than the sixth reference value ΔVb6 (ΔVa2≤ΔVb6), the operation proceeds to step S503, and, whereas if not (ΔVa2>ΔVb6), the present routine is temporarily terminated.

The first period ΔTm1 is set to a period that is relatively long for each measurement cycle of the continuous measurement in the monitoring device 1, e.g., set to a few or several hours through about one day but may be properly changed without being limited to this time range. The sixth reference value ΔVb6 is a threshold value for determining whether or not the glucose concentration of the examinee fluctuates at a small level before and after the elapse of the thus-set first period ΔTm1, and, if the second measurement absolute error ΔVa2 falls within a range of this sixth reference value ΔVb6 or smaller, the fluctuation in glucose concentration is determined to be small.

In step S503, the temperature control unit 13 acquires the CGM measurement value Vcgm (which will hereinafter be termed a "first CGM measurement value Vcgm1") measured at the timing nearest to the measurement time of the first SMBG measurement value Vsmbg1 and the CGM measurement value Vcgm (which will hereinafter be termed a "second CGM measurement value Vcgm2") measured at the timing nearest to the measurement time of the second SMBG measurement value Vsmbg2. Herein, when setting the measurement time of the first CGM measurement value Vcgm1 as the first timing Tm1 and the measurement time of the second CGM measurement value Vcgm2 as the second timing Tm2, the first timing Tm1 is the timing after an elapse of approximately the first period $\Delta Tm1$ from the second timing Tm2. A difference between the elapse period from the second timing Tm2 to the first timing Tm1 and the first period $\Delta Tm1$ is, more or less, said to be a period that is short enough to be ignorable as compared with the first period $\Delta Tm1$.

In step S504, the temperature control unit 13 calculates an absolute value (which will hereinafter be referred to as a "third measurement absolute error $\Delta Va3$") of a difference between the first CGM measurement value Vcgm1 and the second CGM measurement value Vcgm2. Then, the temperature control unit 13 determines whether or not the third measurement absolute error $\Delta Va3$ exceeds a seventh reference value $\Delta Vb7$ (a fourth threshold value). Herein, the seventh reference value $\Delta Vb7$ is a threshold value for determining whether the sensitivity of the glucose sensor 4 is proper or not. If the third measurement absolute error $\Delta Va3$ is equal to or smaller than the seventh reference value $\Delta Vb7$, it is concluded that the sensitivity of the glucose sensor 4 is proper and the glucose concentration contains almost no measurement error. In this step, when determining that the third measurement absolute error $\Delta Va3$ is equal to or smaller than the seventh reference value $\Delta Vb7$ ($\Delta Va3 \leq \Delta Vb7$), it is concluded that the sensitivity of the glucose sensor 4 does not need adjusting specially, and the operation proceeds to step S505. Whereas if the third measurement absolute error $\Delta Va3$ is determined to exceed the seventh reference value $\Delta Vb7$ ($\Delta Va3 > \Delta Vb7$), the operation proceeds to step S506.

In step S506, the temperature control unit 13 changes the setting value of the target setting temperature THtg related to the measurement period of the measurement cycle. Herein, a difference between the measurement values, which is obtained by subtracting the second CGM measurement value Vcgm2 from the first CGM measurement value Vcgm1, is referred to as a "second measurement error $\Delta Vr2$". In this step S506, the change width of the target setting temperature THtg is adjusted corresponding to a magnitude of the second measurement error $\Delta Vr2$. To be specific, the target modified temperature THtgm is calculated by adding the temperature setting change value $\Delta THtg$ obtained by multiplying the second measurement error $\Delta Vr2$ by a constant C4 (where C4>0) to the present target setting temperature THtg (THtgm=THtg+$\Delta THtg$, $\Delta THtg = C4 \times \Delta Vr2$). Note that the calculation formula is an exemplification, and the calculation is not limited to this formula.

Herein, if the second measurement error $\Delta Vr2$ takes the positive value, the temperature setting change value $\Delta THtg$ is modified on the high-temperature side, and hence the sensor sensitivity of the glucose sensor 4 can be enhanced. While on the other hand, if the second measurement error $\Delta Vr2$ takes the negative value, the temperature setting change value $\Delta THtg$ is modified on the low-temperature side, and therefore the sensor sensitivity of the glucose sensor 4 can be lowered. As described above, in the present control example, the change width of the target setting temperature THtg is adjusted corresponding to the magnitude of the second measurement error $\Delta Vr2$, thereby enabling the monitoring device 1 to increase the measurement accuracy of the glucose concentration. Further, if the second CGM measurement value Vcgm2 is higher than the first CGM measurement value Vcgm1, the target setting temperature THtg is modified on the low-temperature side, and it is therefore possible to more surely avoid the occurrence of the deterioration caused by such a point that the temperature of the immobilized enzyme unit 43 of the glucose sensor 4 becomes higher than the optimum temperature zone of the enzyme. Upon finishing the process in this step, the present routine is temporarily terminated.

On the other hand, in step S505, the temperature control unit 13 accesses the aforementioned timer (the illustration is omitted) and thus acquires the second period $\Delta Tm2$ defined as an elapse period reaching the first timing Tm1 since the continuous measurement of the glucose concentration has been started. Subsequently, in step S507, the temperature control unit 13 determines whether or not the second period $\Delta Tm2$ exceeds the predetermined reference period $\Delta Tmb$. The reference period $\Delta Tmb$ is a period serving as a threshold value from which to determine that the immobilized enzyme unit 43 of the glucose sensor 4 does not start getting deteriorated when the continuous usage period of the glucose sensor 4 is within this reference period $\Delta Tmb$. When determining that the second period $\Delta Tm2$ is within the reference period $\Delta Tmb$ ($\Delta Tm2 \leq \Delta Tmb$), the present routine is temporarily terminated in status quo. While on the other hand, when determining that the second period $\Delta Tm2$ exceeds the reference period $\Delta Tmb$ ($\Delta Tm2 > \Delta Tmb$), the operation proceeds to step S508.

In step S508, the temperature control unit 13 changes the setting value of the standby target setting temperature THb during the measurement standby period of each measurement cycle. The change width of the standby target setting temperature THb is adjusted corresponding to a magnitude of the third measurement absolute error $\Delta Va3$. Herein, a standby target modified temperature THbm is calculated by subtracting, from the present target setting temperature THtg, the temperature setting change value $\Delta THb$ obtained by the third measurement absolute error $\Delta Va3$ by a constant C5 (where C5>0) (THbm=THb−$\Delta THb$, $\Delta THb = C5 \times \Delta Va3$). Note that the calculation formula is an exemplification, and the calculation is not limited to this formula.

In this step, the decrease width of the standby target setting temperature THb from the present setting value is set larger with a greater gap quantity between the second CGM measurement value Vcgm2 and the first CGM measurement value Vcgm1, which are obtained by the monitoring device 1 at different two points of timing before and after the first period $\Delta Tm1$. Then, when the second period $\Delta Tm2$ reaching the first timing Tm1 since the continuous measurement of the glucose concentration has been started exceeds the reference period $\Delta Tmb$, the setting value of the standby target setting temperature THb is changed on the low-temperature side, thereby enabling the progress of the deterioration of the glucose sensor 4 to be preferably hindered. Upon finishing the process in this step, the present routine is temporarily terminated.

In the control routine illustrated in FIG. 26, the setting values of both of the target setting temperature THtg and the standby target setting temperature THb are changed based on the gap quantity between the first CGM measurement value Vcgm1 and the second CGM measurement value Vcgm2, however, for instance, an available scheme is that the setting value of any one of the temperatures is changed.

Moreover, a modified example of the control routine shown in FIG. 26 is that the temperature control unit 13, e.g., in step S506, determines before changing the setting value of the target setting temperature THtg whether or not the first CGM measurement value Vcgm1 is smaller than the second CGM measurement value Vcgm2, and, if determined to be affirmative (Vcgm1<Vcgm2), can modify the setting value of the target setting temperature THtg as described above. Then, when determining that the first CGM measurement value Vcgm1 is equal to or larger than the second CGM measurement value Vcgm2 (Vcgm1≥Vcgm2), the present routine may be finished in status quo. If the first CGM measurement value Vcgm1 corresponding to the first timing Tm1 posterior to the second timing Tm2 in time-series is larger than the second CGM measurement value Vcgm2, it is because there is a high possibility that the glucose sensor 4 does not undergo the occurrence of the inconvenience such as the deterioration. Incidentally, in the control example of FIG. 26, it does not happen that the first CGM measurement value Vcgm1 is equal to the second CGM measurement value Vcgm2 in terms of such a relation that the operation proceeds to the process in step S506 if determined to be affirmative in step S504. Alternatively, when determining that the first CGM measurement value Vcgm1 is equal to or larger than the second CGM measurement value Vcgm2 (Vcgm1≥Vcgm2), as explained above, the setting value of the standby target setting temperature THb may be changed as the process in step S508 instead of exiting the present routine. According to this scheme, the deterioration of the glucose sensor 4 can be restrained more surely.

Further, the discussion has been made by exemplifying the case in which the monitoring device 1 according to the present embodiment periodically measures the glucose concentration at the interval of the fixed period of time continuously over, e.g., a few or several days through a few or several weeks, however, this example is no more than the preferable applied example, and the present invention is not limited to this example. Moreover, the monitoring device 1 quantifies the subject substance by measuring the glucose concentration in the body fluid, however, as in the case of determining whether or not the subject substance exists in a fixed region peripheral to the sensor unit of the electrochemical sensor or whether or not the subject substance exceeds a certain level, the present invention can be applied to evaluating the subject substance qualitatively.

Furthermore, the subject substance in the body fluid is not limited to the glucose but may be, e.g., lactic acid and other specified components. In this case, the electrochemical sensor functions as a lactic acid sensor for measuring a lactic acid level, and, e.g., a lactic acid oxidase may be immobilized to the sensor unit (the immobilized enzyme unit) thereof. Moreover, other preferable subject substances can be exemplified such as bile acid. Furthermore, in addition to the enzyme, a microorganism, an antibody and the cell can be preferably applied as the living organism materials retained by the sensor unit of the electrochemical sensor. Further, the present embodiment has discussed the example in which the present invention is applied on the occasion of measuring the numerical value information related to the subject substance in the body fluid of the person (examinee), however, body fluids of other subjects (e.g., animals other than the human being) may, as a matter of course, be used as the samples.

The embodiments of the present invention have been discussed so far, however, the monitoring device, the monitoring system, the monitoring method, the program and the readable-by-computer recording medium recorded with the program are not limited to these embodiments, and the present invention can embrace combinations thereof to the greatest possible degree.

What is claimed is:

1. A monitoring method by which a monitoring device comprising an electrochemical sensor including a sensor unit, for detecting a subject substance in a body fluid, disposed in the way of being embedded subcutaneously, measures numerical value information on the subject substance, said method comprising:
    detecting an ambient temperature with a temperature control unit, said ambient temperature being the temperature ambient to the sensor, and wherein the temperature control unit comprises a temperature sensor and a temperature adjusting element;
    and
    adjusting the ambient temperature with the temperature adjusting element, so as to reach a target setting temperature in the body fluid when measuring the subject substance whereby the temperature control unit controls the operation state of said temperature adjusting element on the basis of the temperature measured by said temperature sensor.

2. A monitoring method according to claim 1, further comprising:
    a determining step of comparing the ambient temperature with the target setting temperature and determining whether a temperature difference between the ambient temperature and the target setting temperature is within a specified range or not; and
    controlling the operation state of the temperature adjusting element for adjusting the ambient temperature so as to approximate the target setting temperature when determining in said determining step that the temperature difference exceeds the specified range,
    wherein the ambient temperature when detecting the subject substance is adjusted, and wherein
    said monitoring method further comprises a calculation step of calculating numerical value information on the subject substance on the basis of an electric signal generated by said electrochemical sensor when determining in said determining step that the temperature difference between the ambient temperature and the target setting temperature is within the specified range.

3. A monitoring method according to claim 2, wherein the ambient temperature is adjusted so as to reach a standby target setting temperature that is set lower than the target setting temperature when standing by for measuring the subject substance.

4. A monitoring method according to claim 2, further comprising comparing a first numerical value information defined as the numerical value information on the subject substance calculated in said calculation step and a second numerical value information defined as the numerical value information on the subject substance measured from the body fluid sampled in vitro from an examinee, and, changing the setting value of the target setting temperature when measuring the subject substance if a difference between the first numerical value information and the second numerical value information exceeds a predetermined first threshold value.

5. A monitoring method according to claim 2, further comprising adjusting the ambient temperature to reach a standby target setting temperature set lower than the target setting temperature when standing by for measuring the subject substance,
    comparing a first numerical value information defined as the numerical value information on the subject substance calculated in said calculation step and a second numerical value information defined as the numerical value information on the subject substance measured from the body fluid sampled in vitro from the examinee, and determining if the difference between the first numerical value information and the second numerical value information exceeds a predetermined second threshold value, wherein if the predetermined second threshold value is exceeded, then changing the setting value of the standby target setting temperature when standing by for measuring the subject substance on a low-temperature side.

6. A monitoring method according to claim 2, further comprising comparing a first numerical value information defined as the numerical value information on the subject substance calculated in said calculation step and a second numerical value information defined as the numerical value information on the subject substance measured from the body fluid sampled in vitro from the examinee, thereby obtaining numerical value information corresponding to a first timing after said monitoring device has started the measurement and the numerical value information corresponding to a second timing that traces back to a predetermined period from the first timing, and changing the setting value of the target setting temperature when measuring the subject substance if a difference between the second numerical value information at the first timing and the second numerical value information at the second timing is within a predetermined third threshold value and if a difference between the first numerical value information at the first timing and the first numerical value information at the second timing exceeds a predetermined fourth threshold value.

7. A monitoring method according to claim 2, further comprising comparing a first numerical value information defined as the numerical value information on the subject substance calculated in said calculation step and a second numerical value information defined as the numerical value information on the subject substance measured from the body fluid sampled in vitro from the examinee, thereby obtaining numerical value information corresponding to a first timing after said monitoring device has started the measurement and the numerical value information corresponding to a second timing that traces back to a predetermined period from the first timing, adjusting the ambient temperature so as to reach a standby target setting temperature that is set lower than the target setting temperature when standing by for measuring the subject substance, and changing the setting value of the standby target setting temperature when standing by for measuring the subject substance on the low-temperature side if an elapse period reaching the first timing since the start of the measurement exceeds a predetermined reference period.

* * * * *